US012084521B2

(12) United States Patent
Toshchakov et al.

(10) Patent No.: US 12,084,521 B2
(45) Date of Patent: Sep. 10, 2024

(54) TLR9 INHIBITORS TO SUPPRESS INFLAMMATORY RESPONSE TO PATHOGENS

(71) Applicant: University Of Maryland, Baltimore, Baltimore, MD (US)

(72) Inventors: Vladimir Toshchakov, Owings Mills, MD (US); Artur Javmen, Baltimore, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 1071 days.

(21) Appl. No.: 16/967,595

(22) PCT Filed: Feb. 6, 2019

(86) PCT No.: PCT/US2019/016900
§ 371 (c)(1),
(2) Date: Aug. 5, 2020

(87) PCT Pub. No.: WO2019/157089
PCT Pub. Date: Aug. 15, 2019

(65) Prior Publication Data
US 2021/0087231 A1 Mar. 25, 2021

Related U.S. Application Data

(60) Provisional application No. 62/626,807, filed on Feb. 6, 2018.

(51) Int. Cl.
*C07K 7/08* (2006.01)
*A61K 38/00* (2006.01)
*C07K 14/705* (2006.01)

(52) U.S. Cl.
CPC ............. *C07K 7/08* (2013.01); *C07K 14/705* (2013.01); *A61K 38/00* (2013.01)

(58) Field of Classification Search
CPC .... C07K 7/08; C07K 14/705; C07K 2319/10; C07K 14/70596; A61K 38/00; A61P 29/00
See application file for complete search history.

(56) References Cited

U.S. PATENT DOCUMENTS

| | | | | |
|---|---|---|---|---|
| 2003/0032090 | A1* | 2/2003 | Hardiman | A61P 35/00 435/325 |
| 2003/0229202 | A1* | 12/2003 | Guo | C12N 15/62 530/350 |
| 2013/0203649 | A1* | 8/2013 | Toshchakov | C07K 14/705 514/21.3 |
| 2016/0039901 | A1 | 2/2016 | Toshchakov | |

FOREIGN PATENT DOCUMENTS

WO 2006111946 A2 10/2006

OTHER PUBLICATIONS

Fekonja (Current Protein and Peptide Science 13.8 (2012): 776-788) (Year: 2012).*
Pan (International journal of molecular sciences 17.2 (2016): 242) (Year: 2016).*
Allette, et al., 2017 Decoy peptide targeted to Toll-IL-1R domain inhibits LPS and TLR4-active metabolite morphine-3 glucuronide sensitization of sensory neurons. Sci Rep 7:3741.
Couture, et al., 2012. Targeting Toll-like receptor (TLR) signaling by Toll/interleukin-1 receptor (TIR) domain-containing adapter protein/MyD88 adapter-like (TIRAP/Mal)-derived decoy peptides. J Biol Chem 287:24641-24648.
Lysakova-Devine, et al., 2010. Viral inhibitory peptide of TLR4, a peptide derived from vaccinia protein A46, specifically Inhibits TLR4 by directly targeting MyD88 adaptor-like and TRIF-related adaptor molecule. J Immunol 185:4261-4271.
Nunez, et al., 2007. A dimer of the Toll-like receptor 4 cytoplasmic domain provides a specific scaffold for the recruitment of signalling adaptor proteins. PloS one 2:e788.
Piao, et al., 2013. Recruitment of TLR adapter TRIF to TLR4 signaling complex is mediated by the second helical region of TRIF TIR domain. Proc Natl Acad Sci U S A 110:19036-19041.
Piao, et al., 2013. Inhibition of TLR4 signaling by TRAM-derived decoy peptides in vitro and in vivo. J Immunol 190:2263-2272.
Piao, et al., 2015. A Decoy Peptide that Disrupts TIRAP Recruitment to TLRs Is Protective in a Murine Model of Influenza. Cell reports 11:1941-1952.
Sarko, et al., 2010. The pharmacokinetics of cell-penetrating peptides. Molecular pharmaceutics 7:2224-2231.
Toshchakov, et al., 2007. Cell-penetrating TIR BB loop decoy peptides a novel class of TLR signaling inhibitors and a tool to study topology of TIR-TIR interactions. Expert opinion on biological therapy 7:1035-1050.
Toshchakov, et al., 2011. Targeting TLR4 signaling by TLR4 Toll/IL-1 receptor domain-derived decoy peptides: Identification of the TLR4 Toll/IL-1 receptor domain dimerization interface. J Immunol 186:4819-4827.

(Continued)

*Primary Examiner* — Nancy J Leith
*Assistant Examiner* — Kyle T Rega
(74) *Attorney, Agent, or Firm* — Wolter Van Dyke Davis, PLLC; Eugene J. Molinelli; Martha Cassidy

(57) ABSTRACT

This invention relates generally to the field of medicine, and particularly to a TLR-9-specific inhibitor peptide effective in vitro and in vivo for modification of inflammatory signaling and host defense pathways. This peptide can be used for TLR-targeting pharmaceutics for treating inflammatory responses caused by various pathogenic and infectious diseases. The invention comprises peptides, peptide fusions, pharmaceutical compositions, and methods for using these compounds and compositions. Peptides of the invention include, but are not limited to SEQ ID NOs:4, 6, 8, 10, 12, 21, or 24, optionally fused to a cell-permeating moiety.

17 Claims, 17 Drawing Sheets

Specification includes a Sequence Listing.

(56) References Cited

OTHER PUBLICATIONS

International Search Report and Written Opinion for International Patent Application No. PCT/US2019/016900 dated Jul. 23, 2019, pp. 1-13.

(Leifer, C et al.) Cytoplasmic Targeting Motifs Control Localization Of Toll-Like Receptor 9. 1, 3-19 Journal of Biological Chemistry. Nov. 17, 2006, Epub Sep. 21, 2006, vol. 281, No. 46; pp. 35585-35592.

(Knezevic, Jet al.) Heterozygous Carriage Of A Dysfunctional Toll-Like Receptor 9 Allele 1, 3-19 Affects CpG Oligonucleotide Responses In B Cells. Journal of Biological Chemistry. Jul. 13, 2012, Epub May 21, 2012, vol. 287, No. 29; pp. 24544-24553.

* cited by examiner

SEQUENCE LISTING

```
<160> NUMBER OF SEQ ID NOS: 39

<210> SEQ ID NO 1
<211> LENGTH: 16
<212> TYPE: PRT
<213> ORGANISM: Drosophila antennapedia
<220> FEATURE:
<221> NAME/KEY: misc_feature
<223> OTHER INFORMATION: cell-permeating peptide vector derived from
      Drosophila antennapedia

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide: 9R1

<400> SEQUENCE: 2

Gly Arg Gln Ser Gly Arg Asp Glu Asp Ala Leu Pro Tyr Asp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide: 9R2
```

```
<400> SEQUENCE: 3

Asp Lys Thr Gln Ser Ala Val Ala Asp Trp Val Tyr Asn Glu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide: 9R3

<400> SEQUENCE: 4

Arg Gly Gln Leu Glu Glu Cys Arg Gly Arg Trp Ala Leu Arg
1               5                   10

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide: 9R3a

<400> SEQUENCE: 5

Arg Gln Ile Lys Ile Trp Phe Gln Asn Arg Arg Met Lys Trp Lys Lys
1               5                   10                  15

Arg Gly Gln Leu Glu Glu Cys Arg Gly Arg Trp Ala Leu Arg
            20                  25                  30

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide: 9R34

<400> SEQUENCE: 6

Gly Arg Trp Ala Leu Arg Leu Cys Leu Glu Glu Arg Asp
1               5                   10

<210> SEQ ID NO 7
<211> LENGTH: 29
<212> TYPE: PRT
<213> ORGANISM: Artificial Sequence
<220> FEATURE:
<223> OTHER INFORMATION: Synthetic peptide: 9R34a

<400> SEQUENCE: 7

Arg Gln Ile Lys Ile Trp Phe Gln Asn Arg Arg Met Lys Trp Lys Lys
1               5                   10                  15

Gly Arg Trp Ala Leu Arg Leu Cys Leu Glu Glu Arg Asp
            20                  25

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide: 9R34-delta-N

<400> SEQUENCE: 8

Ala Leu Arg Leu Cys Leu Glu Glu Arg Asp
1               5                   10

<210> SEQ ID NO 9
<211> LENGTH: 26
```

-continued

```
<212> TYPE: PRT
<213> ORGANISM: Artificial Sequence
<220> FEATURE:
<223> OTHER INFORMATION: Synthetic peptide: 9R34-delta-Na

<400> SEQUENCE: 9

Arg Gln Ile Lys Ile Trp Phe Gln Asn Arg Arg Met Lys Trp Lys Lys
1               5                   10                  15

Ala Leu Arg Leu Cys Leu Glu Glu Arg Asp
            20                  25

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide: 9R34-delta-C

<400> SEQUENCE: 10

Gly Arg Trp Ala Leu Arg Leu Cys Leu Glu
1               5                   10

<210> SEQ ID NO 11
<211> LENGTH: 26
<212> TYPE: PRT
<213> ORGANISM: Artificial Sequence
<220> FEATURE:
<223> OTHER INFORMATION: Synthetic peptide: 9R34-delta-Ca

<400> SEQUENCE: 11

Arg Gln Ile Lys Ile Trp Phe Gln Asn Arg Arg Met Lys Trp Lys Lys
1               5                   10                  15

Gly Arg Trp Ala Leu Arg Leu Cys Leu Glu
            20                  25

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide: 9R34-C/S

<400> SEQUENCE: 12

Gly Arg Trp Ala Leu Arg Leu Ser Leu Glu Glu Arg Asp
1               5                   10

<210> SEQ ID NO 13
<211> LENGTH: 29
<212> TYPE: PRT
<213> ORGANISM: Artificial Sequence
<220> FEATURE:
<223> OTHER INFORMATION: Synthetic peptide: 9R34-C/Sa

<400> SEQUENCE: 13

Arg Gln Ile Lys Ile Trp Phe Gln Asn Arg Arg Met Lys Trp Lys Lys
1               5                   10                  15

Gly Arg Trp Ala Leu Arg Leu Ser Leu Glu Glu Arg Asp
            20                  25

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide: 9R34-delta-L1
```

```
<400> SEQUENCE: 14

Gly Arg Trp Ala Leu Arg Ala Cys Leu Glu Glu Arg Asp
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide: 9R34-delta-L2

<400> SEQUENCE: 15

Gly Arg Trp Ala Leu Arg Ala Cys Ala Glu Glu Arg Asp
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide: 9R4

<400> SEQUENCE: 16

Leu Glu Glu Arg Asp Trp Leu Pro Gly Lys Thr Leu Phe Glu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide: 9R5

<400> SEQUENCE: 17

Asn Leu Trp Ala Ser Val Tyr Gly Ser Arg Lys Thr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic peptide: 9R6

<400> SEQUENCE: 18

His Thr Asp Arg Val Ser Gly Leu Leu Arg Ala Ser Phe Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide: 9R7

<400> SEQUENCE: 19

Leu Ala Gln Gln Arg Leu Leu Glu Asp Arg Lys Asp
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide: 9R8

<400> SEQUENCE: 20
```

Ser Pro Asp Gly Arg Arg Ser Arg Tyr Val Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic peptide: 9R9

<400> SEQUENCE: 21

Arg Tyr Val Arg Leu Arg Gln Arg Leu Cys Arg Gln Ser
1               5                   10

<210> SEQ ID NO 22
<211> LENGTH: 29
<212> TYPE: PRT
<213> ORGANISM: Artificial Sequence
<220> FEATURE:
<223> OTHER INFORMATION: Synthetic peptide: 9R9a

<400> SEQUENCE: 22

Arg Gln Ile Lys Ile Trp Phe Gln Asn Arg Arg Met Lys Trp Lys Lys
1               5                   10                  15

Arg Tyr Val Arg Leu Arg Gln Arg Leu Cys Arg Gln Ser
            20                  25

<210> SEQ ID NO 23
<211> LENGTH: 13
<212> TYPE: PRT
<213> ORGANISM: Artificial Sequence
<220> FEATURE:
<223> OTHER INFORMATION: Synthetic peptide: 9R10

<400> SEQUENCE: 23

Gln Ser Val Leu Leu Trp Pro His Gln Pro Ser Gly Gln
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic peptide: 9R11

<400> SEQUENCE: 24

Arg Ser Phe Trp Ala Gln Leu Gly Met Ala Leu Thr Arg Asp
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Synthetic peptide: 9R11a

<400> SEQUENCE: 25

Arg Gln Ile Lys Ile Trp Phe Gln Asn Arg Arg Met Lys Trp Lys Lys
1               5                   10                  15

Arg Ser Phe Trp Ala Gln Leu Gly Met Ala Leu Thr Arg Asp
            20                  25                  30

<210> SEQ ID NO 26
<211> LENGTH: 14
<212> TYPE: PRT

```
<213> ORGANISM: Artificial Sequence
<220> FEATURE:
<223> OTHER INFORMATION: Synthetic peptide: 9R12

<400> SEQUENCE: 26

Asn His His Phe Tyr Asn Arg Asn Phe Cys Gln Gly Pro Thr
1               5                   10

<210> SEQ ID NO 27
<211> LENGTH: 26
<212> TYPE: PRT
<213> ORGANISM: Artificial Sequence
<220> FEATURE:
<223> OTHER INFORMATION: Synthetic peptide: TR3

<400> SEQUENCE: 27

Arg Gln Ile Lys Ile Trp Phe Gln Asn Arg Arg Met Lys Trp Lys Lys
1               5                   10                  15

Glu Gly Ser Gln Ala Ser Leu Arg Cys Phe
            20                  25

<210> SEQ ID NO 28
<211> LENGTH: 10
<212> TYPE: PRT
<213> ORGANISM: Artificial Sequence
<220> FEATURE:
<223> OTHER INFORMATION: Synthetic peptide: TR3a

<400> SEQUENCE: 28

Glu Gly Ser Gln Ala Ser Leu Arg Cys Phe
1               5                   10

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide: TR5

<400> SEQUENCE: 29

Arg Gln Ile Lys Ile Trp Phe Gln Asn Arg Arg Met Lys Trp Lys Lys
1               5                   10                  15

Glu Leu Cys Gln Ala Leu Ser Arg Ser His Cys Arg
            20                  25

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide: TR5a

<400> SEQUENCE: 30

Glu Leu Cys Gln Ala Leu Ser Arg Ser His Cys Arg
1               5                   10

<210> SEQ ID NO 31
<211> LENGTH: 30
<212> TYPE: PRT
<213> ORGANISM: Artificial Sequence
<220> FEATURE:
<223> OTHER INFORMATION: Synthetic peptide: TR6

<400> SEQUENCE: 31

Arg Gln Ile Lys Ile Trp Phe Gln Asn Arg Arg Met Lys Trp Lys Lys
1               5                   10                  15
```

```
Pro Phe Gly Leu Arg Asp Pro Trp Cys Lys Tyr Gln Met Leu
            20                  25                  30

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide: TR6a

<400> SEQUENCE: 32

Pro Phe Gly Leu Arg Asp Pro Trp Cys Lys Tyr Gln Met Leu
1               5                   10

<210> SEQ ID NO 33
<211> LENGTH: 30
<212> TYPE: PRT
<213> ORGANISM: Artificial Sequence
<220> FEATURE:
<223> OTHER INFORMATION: Synthetic peptide: TR9

<400> SEQUENCE: 33

Arg Gln Ile Lys Ile Trp Phe Gln Asn Arg Arg Met Lys Trp Lys Lys
1               5                   10                  15

Ala Ala Tyr Pro Pro Glu Leu Arg Phe Met Tyr Tyr Val Asp
            20                  25                  30

<210> SEQ ID NO 34
<211> LENGTH: 14
<212> TYPE: PRT
<213> ORGANISM: Artificial Sequence
<220> FEATURE:
<223> OTHER INFORMATION: Synthetic peptide: TR9a

<400> SEQUENCE: 34

Ala Ala Tyr Pro Pro Glu Leu Arg Phe Met Tyr Tyr Val Asp
1               5                   10

<210> SEQ ID NO 35
<211> LENGTH: 29
<212> TYPE: PRT
<213> ORGANISM: Artificial Sequence
<220> FEATURE:
<223> OTHER INFORMATION: Synthetic peptide: TR11

<400> SEQUENCE: 35

Arg Gln Ile Lys Ile Trp Phe Gln Asn Arg Arg Met Lys Trp Lys Lys
1               5                   10                  15

Gly Gly Phe Tyr Gln Val Lys Glu Ala Val Ile His Tyr
            20                  25

<210> SEQ ID NO 36
<211> LENGTH: 13
<212> TYPE: PRT
<213> ORGANISM: Artificial Sequence
<220> FEATURE:
<223> OTHER INFORMATION: Synthetic peptide: TR11a

<400> SEQUENCE: 36

Gly Gly Phe Tyr Gln Val Lys Glu Ala Val Ile His Tyr
1               5                   10

<210> SEQ ID NO 37
<211> LENGTH: 13
<212> TYPE: PRT
```

```
<213> ORGANISM: Artificial Sequence
<220> FEATURE:
<223> OTHER INFORMATION: Synthetic peptide: 4R9

<400> SEQUENCE: 37

Leu Arg Gln Gln Val Glu Leu Tyr Arg Leu Leu Ser Arg
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic peptide: 2R9

<400> SEQUENCE: 38

Pro Gln Arg Phe Cys Lys Leu Arg Lys Ile Met Asn Thr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic peptide: 4-alpha-E

<400> SEQUENCE: 39

His Ile Phe Trp Arg Arg Leu Lys Asn Ala Leu Leu Asp
1               5                   10
```

TLR9 INHIBITORS TO SUPPRESS INFLAMMATORY RESPONSE TO PATHOGENS

GOVERNMENT FUNDING SUPPORT

This invention was made with government support under grant no. AI-082299 awarded by the National Institutes of Health. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "20190325_15024356PC0_ST25" created on Mar. 25, 2019 and is 11,052 bytes in size. The sequence listing contained in this .txt file is part of the specification and is hereby incorporated by reference herein in its entirety.

CROSS-REFERENCE TO RELATED APPLICATIONS

This application is a § 371 of international patent application WO 2019/157089 (PCT/US2019/016900), filed 6 Feb. 2019, claims the benefit of U.S. provisional application Ser. No. 62/626,807, filed 6 Feb. 2018. The entire contents of this application is hereby incorporated by reference as if fully set forth herein.

BACKGROUND

1. Field of the Invention

This invention relates generally to the fields of medicine and veterinary medicine, and particularly to Toll-like receptor (TLR)-9-specific inhibitor peptides effective in vitro and in vivo for modification of inflammatory signaling elicited by agonists of TLR9. This peptide and modifications of the peptide can be used as TLR-targeting pharmaceutics for treating inflammatory responses caused by various pathogenic or infectious agents.

2. Background of the Invention

Toll-like receptors (TLRs) are an evolutionarily conserved protein family that function as "pattern recognition receptors" (PRR) to recognize conserved microbial molecules, also called pathogen-associated molecular patterns (PAMPs), as well as endogenous ligands associated with inflammation and tissue injury, which are called danger-associated molecular patterns (DAMPs). TLRs thus sense a variety of conserved molecules. These receptors play an important role in the initiation and maintenance of the inflammatory response to pathogens that enables the host to combat infection. However, excessive or prolonged TLR signaling is a pathogenic factor in many inflammatory and autoimmune diseases. The human genome encodes 10 TLRs, termed TLR1, TLR2, TLR3, etc. Upon ligand binding, the receptors generally homodimerize, although TLR2 forms heterodimers with TLR1 or TLR6, with each dimer having a different ligand specificity.

Each of the TLRs is structurally similar, consisting of an extracellular leucine-rich repeat domain, a membrane-spanning helix, and a cytosolic TIR (Toll/IL-1 Receptor) domain. Upon recognition of either a pathogen-associated molecular pattern (PAMP) or damage-associated molecular pattern (DAMP) ligand, the ectodomains of stimulated TLRs form an M-shaped structure in which the C-termini of ectodomains converge, leading to dimerization of cytosolic TIR domains. TIR dimerization exposes a composite binding site which provides a surface for recruitment of downstream TIR-domain containing adapter molecules present in the cytoplasm that, in turn, trigger signal propagation. Complementary surface areas of TIR domains, called interfaces, are key for the signal-initiated mutual recognition of TIR-containing proteins and the assembly of functional TLR signaling complexes through TIR:TIR domain interaction. TIR domains do not have a common TIR-binding motif and can interact via structurally distinct regions with several TIRs simultaneously.

Toll-like receptors have different cellular localization. TLR1, TLR2, TLR4, TLR5, and TLR6 are located at the plasma membrane. These TLRs recognize microbial lipids, lipopeptides, and proteins; TLR3, TLR7, TLR8, TLR9, and TLR13 are located in intracellular compartments and recognize nucleic acids; and TLR1 and TLR12 are endosomally expressed and recognize bacterial proteins. Agonists of TLR10 remain unknown. TLR9 is activated by DNA sequences that contain unmethylated CpG motifs, typical for bacterial and viral DNA.

TLRs are type I transmembrane receptors that initiate intracellular signaling through Toll/Interleukin-1R homology domains (TIR). Activated TLRs dimerize and bring their TIR domains to direct physical contact. The TIR dimers subsequently recruit TIR domain-containing adapter proteins through TIR-TIR interactions. Adapter protein recruitment to activated TLRs governs the specificity of the TLR response. There are four recognized TIR-containing TLR adapter proteins: MyD88, TIRAP/Mal, TRIF, and TRAM. Toll/interleukin-1 receptor domain-containing adapter protein (TIRAP), also known as MyD88-adapter-like (Mal), is a TIR domain-containing adapter that facilitates recruitment of MyD88 (a second adapter protein) to certain TLRs and, thereby activates NF-κB. In the case of TLR4, there are two signaling pathways: MyD88-dependent and independent. The MyD88-dependent pathway utilizes TIRAP to bridge TLR4 and MyD88. The MyD88-independent pathway uses a third adapter protein, TRAM (TIR domain-containing adapter-inducing interferon-β- (TRIF-) related adapter molecule), which bridges TRIF (the fourth adapter protein) and allows for activation of IRF3. TIRAP appears to share a binding site with TRAM located at the TLR4 TIR homodimer.

TIR domains, whether in the TLRs or the adapter proteins, mediate transient receptor-adapter interactions, eliciting the inflammatory signaling and antimicrobial host defense. TIR domains tend to interact with other TIR domains, yet functional TIR:TIR interactions are specific, as exemplified by the recruitment of specific TIR-containing adapter proteins in response to activation of a particular receptor. Some TIR-containing adapter proteins participate in multiple signaling pathways, while others interact with a smaller set of proteins. For example, MyD88 is a necessary adapter for all members of the IL-1R family and all TLRs with the exception of TLR3, whereas TIRAP participates in a smaller TLR subset. Despite considerable effort, the molecular mechanisms that determine specificity of TIR:TIR interactions are not completely understood.

Recruitment of MyD88 to TLRs promotes the assembly of myDDosomes, signaling complexes formed by death domains of MyD88, IRAK.4, and IRAK2. MyDDosome formation activates IRAKs, leading to the activation of NF-κB. TLR4 and TLR3 can also engage TRIF, leading to the formation of triffosomes and activation of interferon-regulatory factor-3 (IRF). TIRAP and TRAM, often referred to as bridging adapters, stabilize TLR TIR dimers and facilitate recruitment of MyD88 and TRIF, respectively. TIRs are alpha/beta protein domains, the core of which is formed by the central, typically 5-stranded, parallel β-sheet, surrounded by 5 α-helices. TIR domains can interact through structurally diverse regions. For instance, TLR2 TIR alpha-helix D interacts with TIRAP, whereas its AB loop is involved in receptor dimerization.

The small size (3-3.5 nm) and generally globular shape of TIR domains implies that any binary TIR:TIR complex has a limited interface size, typically less than 900 Å, and therefore a binary TIR complex is relatively weak and unstable. The stability of receptor complexes is achieved through a simultaneous, cooperative interaction of several (more than two) TIR domains, and multiple interface sites are expected in each TIR domain involved in signaling. Although the general mechanism of TLR signaling complex assembly and the architecture of TLR signaling complexes are common for most of TLRs, the specific interface sites within TIR domains that mediate proteins interactions required for signaling complex assembly often differs in individual TIR domains.

Involvement of TLRs in the development of rheumatoid arthritis, atherosclerosis, systemic lupus erythematosus and systemic sclerosis and the potential of TLR antagonists in the treatment of inflammatory diseases has been extensively discussed in the literature.

Libraries of cell-permeable decoy peptides (CPDP) derived from the TIR domains of many TLRs and their adapters have been screened-several TLR inhibitors that have different specificities and dissimilar sequences were identified. The anti-inflammatory properties of several of these peptides were independently confirmed. Previous work has shown a potent anti-inflammatory effect of TIRAP-derived peptide TR6 in a mouse model of LPS-induced mastitis. The protective action of TRAM-derived peptide TM6 has been demonstrated in LPS-induced acute lung injury. TLR4-derived peptide 4BB decreased the effects of LPS on calcium fluxes and neuronal excitability. Although several other groups have reported analogous TLR inhibitory peptides from bacterial and viral proteins, no inhibitor that targets TLR9 TIR domain has been reported to date.

The common, N-terminal part of a CPDP is the cell-permeating peptide vector derived from *Drosophila antennapedia* (referred to herein as antennapedia) homeodomain (RQIKIWFQNRRMKWKK; SEQ ID NO:1). This vector is effective for intracellular delivery of cargoes of diverse size and chemical nature in cell culture and small animal models. The C-terminal half of a CPDP is a segment of TIR domain primary sequence that represents a particular, non-fragmented patch of TIR domain surface that might serve as a TIR-TIR interface. The TLR9 TIR libraries were designed in such a way that all peptides in a library collectively represent the entire surface of the TLR9 TIR.

Control of innate immunity in response to infection is vitally important as an impaired response increases susceptibility to infection, while an uncontrolled response can lead to inflammatory disease or lethality. TLRs and adapter proteins are important therapeutic targets because excessive TLR signaling is a pathogenic mechanism in many inflammatory diseases, including sepsis, while too little TLR signaling can produce a lack of sufficient immune activity in response to attack. Thus, there is a need in the art for new methods to modulate TLR in the field of medicine.

SUMMARY OF THE INVENTION

The present invention identifies new CPDP inhibitors of TLR9. The most potent inhibitory peptide of the TLR9 TIR library, 9R34, and its modifications, including 9R34-ΔN, are derived from the surface-exposed segment of TLR9 TIR that includes AB loop, β-strand B, and N-terminal residues of BB loop. Peptides from α-helices E and D, 9R11 and 9R9, also inhibited TLR9, but were less potent. The cell-based binding assay has demonstrated that 9R34-ΔN binds TLR9 TIR domain and, with a slightly lower affinity, TIRAP TIR. 9R34-ΔN, inhibited systemic cytokine activation induced in mice by ODN1668 and protected D-galactosamine (D-gal) pretreated mice against TLR9-induced lethality. Presented results identify novel TLR9 inhibitors and provide new insights into the molecular mechanisms of TLR9 signaling.

The invention therefore relates to defined linear epitopes/binding sites within TIR domains of TLRs and TLR adapter proteins that mediate TIR domain interactions required for the assembly of TLR signaling complexes and TLR function. An important feature of these identified epitopes is that when a mimic of an epitope, such as a peptide or related molecule, is delivered to cells, it can block functional interactions of TIR domains through a competitive mechanism and, in some cases, inhibit or modify signaling initiated by a TLR.

In particular, the invention relates to a peptide selected from the group consisting of SEQ ID NOs:4, 6, 8, 10, 12, 21, and 24, and variants thereof having one or two amino acid changes, independently selected from additions, substitutions and deletions, in the TIR-domain segment of the peptide, wherein the peptide optionally is fused with a cell permeating peptide vector or a variant thereof having one or two amino acid changes, independently selected from additions, substitutions and deletions. Preferably, the peptide is selected from the group consisting of SEQ ID NOs:6, 8, 10, and 12, and variants thereof having one or two amino acid changes, independently selected from additions, substitutions and deletions, in the TIR-domain segment of the peptide, wherein the peptide optionally is fused with a cell permeating peptide vector or a variant thereof having one or two amino acid changes, independently selected from additions, substitutions and deletions.

Preferred peptides are those wherein the peptide is fused with a cell permeating peptide vector or a variant thereof having one or two amino acid changes, independently selected from additions, substitutions and deletions, and most preferably, the cell permeating peptide vector is SEQ ID NO:1. Additional preferred peptides therefore include peptides selected from the group consisting of SEQ ID NOs:5, 7, 9, 11, 13, 22, and 25.

The invention also relates to pharmacological compositions comprising a pharmaceutically acceptable excipient and any of these peptides, including SEQ ID NOs:4, 6, 8, 10, 12, 21, and 24, preferably fused to a cell permeating peptide vector, most preferably the antennapedia cell permeating peptide vector, such as SEQ ID NOs:5, 7, 9, 11, 13, 22, and 25.

In addition, the invention relates to a method of inhibiting TIR:TIR interaction between two TIR (Toll/IL-1 receptor) domain-bearing proteins, comprising contacting a cell expressing TIR domain-bearing proteins with one or more of the peptides discussed herein and above. The methods preferably are those wherein the TIR domain-bearing proteins are TLRs, or TLR adapter proteins, or both, and preferably wherein the TLR is TLR9 and/or the TLR adapter protein is TIRAP.

The invention also includes a method of treating a subject in need, comprising administering to the subject a therapeutically effective amount of a pharmaceutical composition comprising the peptides of discussed herein, wherein the subject suffers from an inflammatory or genetic disease promoted by TLR activation which exacerbates or causes the disease. Further, the invention also includes a method of treating a subject in need, comprising administering to the subject a therapeutically effective amount of a pharmaceutical composition comprising the peptides discussed herein, wherein the subject suffers from an inflammatory or genetic disease promoted by TLR activation which exacerbates or causes the disease. The inflammatory or genetic disease promoted by TLR activation can be a condition selected from the group consisting of inflammation, generalized infection or sepsis, septic shock, autoimmune disease, systemic lupus erythematosis, multiple sclerosis, plaque psoriasis, rheumatoid arthritis, graft versus host disease, arthritis, Sjogren's syndrome, cancer, viral infection, transplant rejection, and reactions to antimalarials and/or antipsoriatics.

BRIEF DESCRIPTION OF THE FIGURES

FIG. 1C presents schematics of adapter recruitment to activated TLR9. FIG. 1D presents schematics of MyD88 recruitment to activated TLR9 in the absence of TIRAP. FIG. 1E and FIG. 1F show TLR2/1 and TLR2/6 signaling filament elongation models.

FIG. 5B, IL-10; FIG. 5C, IL-12-p40; and FIG. 5D, IL-6) following macrophage stimulation with ODN 1668.

DETAILED DESCRIPTION

1. Definitions

Figure 1:
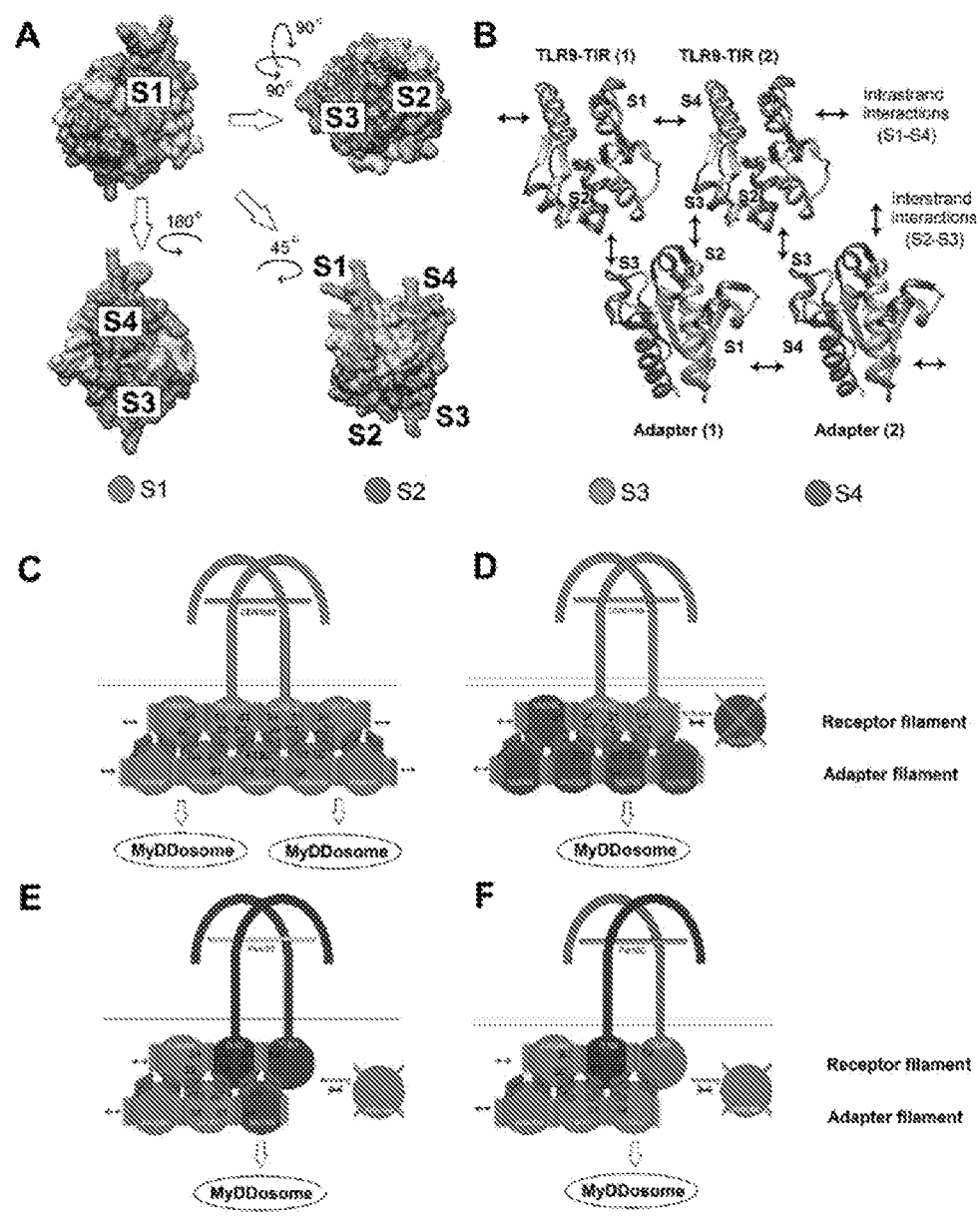
FIG. 1A presents four TIR surfaces (S1-S4) that mediate the assembly of primary TLR signaling complexes. Surface 1 (S1) (yellow highlight) and Surface 4 (S4) (orange highlight) are located on opposite TIR sides, near β-strands B and E, the strands that form lateral, surface-exposed edges of the β-sheet. Surface 2 (S2) (shown in green) is formed by α-helices B and C, whereas Surface 3 (dark blue) is formed by α-helix D and may include adjacent loops.
FIG. 1B illustrates that, in the context of TLR signaling complexes, Surface 1 (S1) interacts with Surface 4 (S4), while S2 interacts with S3 to form a double-stranded, open-ended filamentous structure.
FIG. 1C, FIG. 1D, FIG. 1E and FIG. 1F present variants of signaling complexes formed through S1-S4 and S2-S3 interactions of TLR and TLR adapter TIRs.

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

Abbreviations used herein include: BMDM, bone marrow-derived macrophages; Cer, Cerulean; CPDP, cell-permeating decoy peptides; D-Gal, D-galactosamine; FLIM, fluorescence lifetime imaging; LPS, lipopolysaccharide; ODN, oligonucleotide; pdb, protein database file; TIR, Toll/IL-1R homology domain, TIRAP, TIR domain-containing adapter protein, also known as Mal; TRIF, TIR domain-containing adapter inducing IFN-0; TRAM, TRIF-related adapter molecule.

As used herein, "a" or "an" may mean one or more than one. As used herein when used in conjunction with the word "comprising," the words "a" or "an" may mean one or more than one. As used herein "another" may mean at least a second or more. Unless otherwise required by context, singular terms include pluralities and plural terms include the singular.

The term "about," as used herein, means plus or minus 20 percent of the recited value, so that, for example, "about 0.125" means 0.125±0.025, and "about 1.0" means 1.0±0.2. In some instances, the term "about" may include numerical values that are rounded to the nearest significant figure.

As used herein, the terms "treat", "treating" and "treatment" include improving, reducing, or eliminating a disease or condition or a symptom of a disease or condition; slowing or reversing the progression of a disease or condition or a symptom of a disease or condition; decreasing the severity and/or frequency of the occurrence of a disease or condition or a symptom of a disease or condition; and preventing, lessening the severity of, or lessening the chance of the occurrence or recurrence of a disease or condition or a symptom of a disease or condition.

In general, treatment refers to ameliorating, blocking, reducing, decreasing or inhibiting a disease condition or symptom by about 1% to about 100% compared to a subject to which the peptides and/or compositions of the present invention have not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% compared a subject to which the peptides or compositions have not been administered.

As used herein, the term TIR "domain peptide" refers to a peptide that correspond to a generally surface-exposed segment of TIR domain primary sequence of a TLR or TLR adapter, and includes the peptides listed in Tables 1 and 2. Such peptides are considered part of the invention described herein.

As used herein, the term "decoy peptide" refers to cell permeating decoy peptides (CPDP) comprised of a cell-permeable peptide vector and a TIR domain peptide. Such peptides are considered part of the invention described herein. A CPDP, for example, is a cell permeating peptide vector at the N-terminus, fused to a segment of TIR domain primary sequence (a TIR "domain peptide") that represents a particular, non-fragmented patch of TIR domain surface that might serve as a TIR-TIR interface, at the C-terminus. Preferably, the cell permeating peptide is the antennapedia sequence RQIKIWFQNRRMKWKK; SEQ ID NO:1. Other suitable cell-permeating peptides include Herpes simplex virus 1 (HSV-1) protein VP22 and trans-activating transcriptional activator (TAT) from HIV-1, however any cell permeating or cell penetrating peptides known in the art is suitable for use with the domain peptides of the invention.

While the examples provide herein place the cell-permeating peptide at the amino terminal end of the decoy peptides, depending on the identity of the cell-permeating peptide it may also be placed at the carboxy terminus of the decoy peptides.

As used herein, the term "MyD88 TIR domain" refers to the TIR domain of myeloid differentiation primary response protein MyD88 (*Homo sapiens*) (NCBI Reference Sequence: NP_001166038.2) or its orthologue.

As used herein, the term "TIRAP TIR domain" refers to the TIR domain of toll/interleukin-1 receptor domain-containing adapter protein (*Homo sapiens*) (NCBI Reference Sequence: NP_001034750.1) or its orthologue.

As used herein, the term "TRAM TIR domain" refers to the TIR domain of TIR domain-containing adapter molecule 2(*Homo sapiens*) (NCBI Reference Sequence: NP_067681.1) or its orthologue.

As used herein, the term "TRIF TIR domain" refers to the TIR domain of TIR domain-containing adapter molecule 1 (*Homo sapiens*) (NCBI Reference Sequence: NP_891549.1) or its orthologue.

As used herein, the term "TLR9 TIR domain" refers to the TIR domain of Toll-like receptor 9 (NCBI Reference Sequence: NP_059138.1) or its orthologues.

As used herein, the term "TLR adapter protein" may refer to TIRAP, MyD88, TRAM, or TRIF; however when the term refers the TLR9 adapters specifically, the referred adapters are MyD88 and TIRAP.

As used herein, the term "ODN 1668" refers to the synthetic phosphorothioate oligonucleotide that contains unmethylated CpG dinucleotides in the context of the 5'-tc-catgacgttcctgatgct-3' sequence.

As used herein, the term "competitive TLR inhibitor" refers to a TLR inhibitor that binds same binding site as the agonists of that particular TLR and thus "competes" for the binding site with the TLR agonist.

As used herein, the term "cell permeating peptide vector" refers to a peptide sequence that can transport a peptide across the cell membrane. Preferably, the cell permeating peptide is the antennapedia sequence RQIKIWFQNRRMKWKK; SEQ ID NO:1. Other suitable cell-permeating peptides include Herpes simplex virus 1 (HSV-1) protein VP22 and trans-activating transcriptional activator (TAT) from HIV-1, however any cell permeating or cell penetrating peptides known in the art is suitable for use with the domain peptides of the invention.

2. Embodiments of the Invention

TIR domains are common structural units of many signaling proteins. These domains mediate the signal-dependent formation of oligomeric protein complexes through homo- and heterotypic TIR-TIR interactions. TIR domains do not have a common binding sequence motif notwithstanding the generally common structure and function. Similarity in the group is limited to only 20-30%. The absence of a common TIR-TIR binding motif presents an opportunity to specifically target particular interfaces within TIR domains. One approach to developing protein interaction inhibitors uses the ability of short peptides derived from protein interaction sites to block protein interactions mediated by this site. Here, a peptide library derived from the TLR9 TIR for dominant-negative effect on TLR9 signaling was examined to extend knowledge of peptides from TIR domains and their adapters and co-receptors. The library of TLR9 peptides was designed similarly to TLR and TLR adapter peptide libraries tested previously. Each peptide in the library corresponds to a short segment of TLR9 sequence that presumably forms a non-fragmented patch of TIR surface. All peptides of the library together encompass the entire surface of TLR9 TIR. Therefore, each TIR-derived peptide represents a patch of TIR surface that might mediate a TIR-TIR interaction within the primary receptor complex. See Table 1, below and FIG. 1. This study primarily examines a peptide library derived from the TLR9 TIR for a dominant-negative effect on TLR9 signaling.

Putative TIR interaction sites and the modes of TIR domain interactions in TLR signaling complexes are shown as follows. Four TIR surfaces (S1-S4) that mediate the assembly of primary TLR signaling complexes are shown in FIG. 1A. Surface 1 (S1) (yellow highlight) and Surface 4 (S4) (orange highlight) are located on opposite TIR sides, near β-strands B and E, the strands that form lateral, surface-exposed edges of the β-sheet. Surface 2 (S2) (shown in green) is formed by α-helices B and C, whereas Surface 3 (dark blue) is formed by α-helix D and may include adjacent loops. In the TLR9 peptide set, S1, S3, and S4 are represented by peptide 9R34, 9R9, and 9R11, respectively; whereas of peptides that should jointly form S2, i.e., 9R5 and 9R6, only 9R6 inhibited weakly. The images show a homology model of TLR9 TIR computationally built using TLR2 TIR protein database file (pdb) (pdb ID: 1O77) as a template.

FIG. 1B shows domain interactions that initiate intracellular TLR signaling. Two upper TIR domains of this panel represent dimerized receptor TIR domains; whereas the two lower TIRs represent adapters. The upper TIRs show the same TLR9 TIR model as in FIG. 1A, but in the ribbon style. The two lower TIRs are representations of TIRAP TIR model (pdb ID: 5UZB, chain A). S1 and S4 mutually interact to mediate the intrastrand TIR-TIR interactions of the complex. S1 and S4 of TLR TIRs form receptor dimers. These Surfaces also may recruit adapters through lateral, intrastrand interactions, thereby leading to elongation of the complex in either one or two directions. Color coding of TIR segments in FIG. 1B correspond to that in FIG. 1A.

S2 interacts with S3, forming the interstrand interactions. S2 and S3 are located on the same TIR hemisphere; these surfaces mediate interstrand receptor-adapter and adapter-adapter interactions (only receptor-adapter S2-S3 interactions are shown in FIG. 1B). Surfaces 2 and 3 of one TIR domain interact with cognate surfaces of two separate TIR domains of the opposite strand in the cooperative mode.

TLR9 TIR dimers recruit adapters through intrastrand and interstrand interactions. See FIG. 1C. The TLR9 TIR complex elongates bidirectionally in the presence of both TIRAP and MyD88. Bidirectional elongation of TLR9 signaling protofilaments is possible due to ability of TLR9 S1 to interact with TIRAP and the ability of TLR9 S4 to bind either TIRAP or MyD88. Adapter-adapter S2-S3 interstrand interactions occur after elongation of the receptor filament through intrafilament S1-S4 interactions. In the absence of TIRAP, the TLR9 filaments elongate unidirectionally only through S4 surface of the dimer. See FIG. 1D.

FIG. 1E and FIG. 1F show TLR2/1 and TLR2/6 signaling filament elongation models. TLR2 filaments elongate unidirectionally because S1 of both TLR2 coreceptors are inept in binding the TLR2 adapters. Strong TIRAP-dependence of TLR2 signaling is due to high affinity TLR2-TIRAP interaction through S3 of TLR2.

TABLE 1

Sequences of TLR9 TIR-derived domain and decoy peptides.

| Peptide | Sequence | SEQ ID NO | Prototype/Main Structural Element |
| --- | --- | --- | --- |
| 9R1 | GRQSGRDEDALPYD | 2 | N-terminal segment |
| 9R2 | DKTQSAVADWVYNE | 3 | AA loop, α-helix A |
| 9R3 | RGQLEECRGRWALR | 4 | α-helix A, AB loop |
| 9R3a | RQIKIWFQNRRMKWKKRGQLEECRGRWALR | 5 | |
| 9R34 | GRWALRLCLEERD | 6 | AB loop, β-strand B, |
| 9R34a | RQIKIWFQNRRMKWKKGRWALRLCLEERD | 7 | N-terminal residues of BB loop |
| 9R34-ΔN | ALRLCLEERD | 8 | AB loop, β-strand B, |
| 9R34-ΔNa | RQIKIWFQNRRMKWKKALRLCLEERD | 9 | BB loop |
| 9R34-ΔC | GRWALRLCLE | 10 | AB loop, β-strand B |
| 9R34-ΔCa | RQIKIWFQNRRMKWKKGRWALRLCLE | 11 | |
| 9R34-C/S | GRWALRLSLEERD | 12 | AB loop, β-strand B, |
| 9R34-C/Sa | RQIKIWFQNRRMKWKKGRWALRLSLEERD | 13 | BB loop |
| 9R34-ΔL1 | GRWALRACLEERD | 14 | AB loop, β-strand B, BB loop |
| 9R34-ΔL2 | GRWALRACAEERD | 15 | AB loop, β-strand B, BB loop |
| 9R4 | LEERDWLPGKTLFE | 16 | β-strand B, BB loop, α-helix B |
| 9R5 | NLWASVYGSRKT | 17 | α-helix B, BC loop, β-strand C |
| 9R6 | HTDRVSGLLRASFL | 18 | α-helix C |

TABLE 1-continued

Sequences of TLR9 TIR-derived domain and decoy peptides.

| Peptide | Sequence | SEQ ID NO | Prototype/Main Structural Element |
|---------|----------|-----------|-----------------------------------|
| 9R7 | LAQQRLLEDRKD | 19 | α-helix C, CD loop, β-strand D |
| 9R8 | SPDGRRSRYVR | 20 | DD loop, α-helix D |
| 9R9 | RYVRLRQRLCRQS | 21 | α-helix D, DE loop |
| 9R9a | RQIKIWFQNRRMKWKKRYVRLRQRLCRQS | 22 | |
| 9R10 | QSVLLWPHQPSGQ | 23 | DE loop, β-strand E, EE loop |
| 9R11 | RSFWAQLGMALTRD | 24 | α-helix E |
| 9R11a | RQIKIWFQNRRMKWKKRSFWAQLGMALTRD | 25 | |
| 9R12 | NHHFYNRNFCQGPT | 26 | C-terminal segment |
| TR3 | RQIKIWFQNRRMKWKKEGSQASLRCF | 27 | AB loop and a part of strand B |
| TR3a | EGSQASLRCF | 28 | |
| TR5 | RQIKIWFQNRRMKWKKELCQALSRSHCR | 29 | Second helical region of TIRAP TIR (helix B) |
| TR5a | ELCQALSRSHCR | 30 | |
| TR6 | RQIKIWFQNRRMKWKKPFGLRDPWCKYQML | 31 | Third helical region of TIRAP TIR (helix 32C) |
| TR6a | PFGLRDPWCKYQML | 32 | |
| TR9 | RQIKIWFQNRRMKWKKAAYPPELRFMYYVD | 33 | Fourth helical region of TIRAP TIR (helix D) |
| TR9a | AAYPPELRFMYYVD | 34 | |
| TR11 | RQIKIWFQNRRMKWKKGGFYQVKEAVIHY | 35 | Fifth helical region of TIRAP TIR (helix E) |
| TR11a | GGFYQVKEAVIHY | 36 | |
| 4R9 | LRQQVELYRLLSR | 37 | α-helix D, DE loop of TLR4 TIR |
| 2R9 | PQRFCKLRKIMNT | 38 | α-helix D, DE loop of TLR2 TIR |
| 4αE | HIFWRRLKNALLD | 39 | α-helix E of TLR4 TIR |

Screening results have suggested that TLR9 decoy peptides 9R3, 9R34, 9R9, and 9R11, all inhibit TLR9 signaling. These peptides represent TIR surfaces, S1, S3, and S4, respectively (see FIG. 1A). Only one of the putative S2 peptides, 9R6, weakly inhibited.

TLR9 inhibitory peptides represent three non-contiguous surface regions of TLR9 TIR (see FIG. 2B). Comparison of the location of inhibitory segments in the TLR9 peptide library with that of previously screened libraries derived from other TLRs suggests that the location of TIR segments capable of blocking TIR-TIR interactions is generally conserved in TLRs, yet there are important differences. Thus, TLR9 peptide derived from the AB loop, i.e., Region 3, was inhibitory, whereas the BB loop peptide (9R4) did not inhibit (see FIG. 3).

The TLR sets differed in the inhibitory ability of the BB loop peptides (these peptides were designated as Region 4 peptides). This region is sequentially consecutive and represents a contiguous surface region to Region 3 (FIG. 2A). Whereas TLR4 and TLR2 BB loop decoy peptides inhibited cognate signaling, TLR1, TLR6, and TLR9 BB loop peptide did not inhibit.

Figure 3:
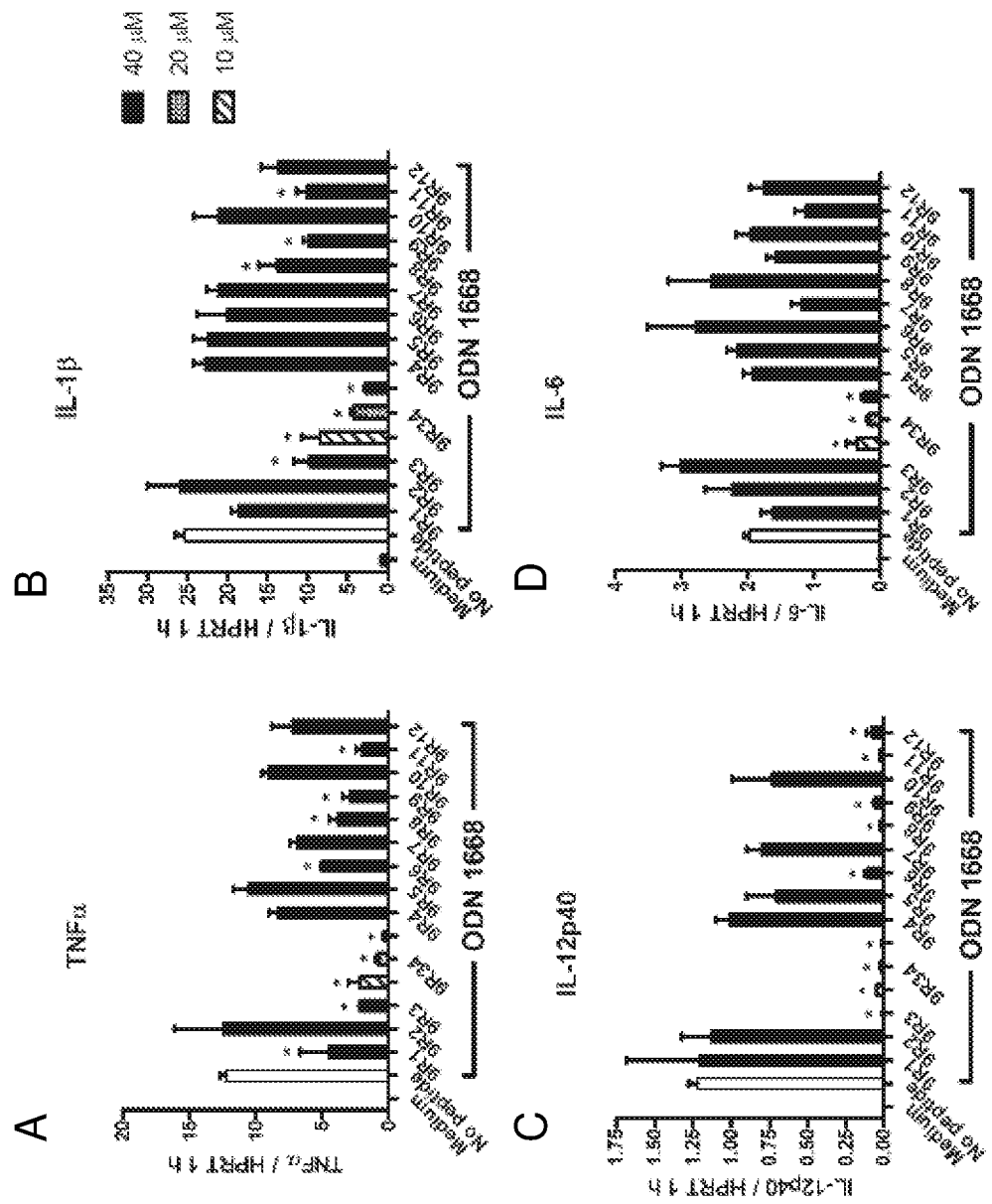
FIG. 3A, FIG. 3B, FIG. 3C and FIG. 3D are bar graphs showing expression of TNFα, IL-10, IL-12-p40, and IL-6 mRNA, respectively, by cells stimulated with TLR9 agonist ODN1668 and treated with various peptides or mock treated.

In the TLR9 set, the BB loop peptide did not inhibit signal transduction, but peptides derived from the region centered on the border between Regions 3 and 4, peptides 9R34 and 9R34-ΔN, inhibited TLR9 signaling more potently than 9R3 (see FIG. 3). However, peptides from the AB or BB loop of TLR2 co-receptors did not inhibit the TLR2-mediated signaling. All inhibitory peptides derived from Region 3 or 4 of a TLR targeted the TLR TIR of the corresponding dimerization partner, suggesting that this region may serve as the receptor dimerization surface. Thus, binding of TLR4 BB loop peptide, 4BB, to TLR4 TIR was demonstrated in a cell-based FRET assay. In decoy peptide sets from TLRs that heterodimerize, i.e., TLR2 and TLR1 or TLR6, the TLR2 peptide, 2R3, inhibited, but structurally homologous peptides from TLR1 and TLR6 were inert. Peptide binding studies have suggested that both TLR4-derived peptides, 4R3 and 4R4, bind TLR4 TIR domain. Analogously, the TLR2-derived 2R3 co-immunoprecipitated with TLR1 and TLR6.

Figure 11:
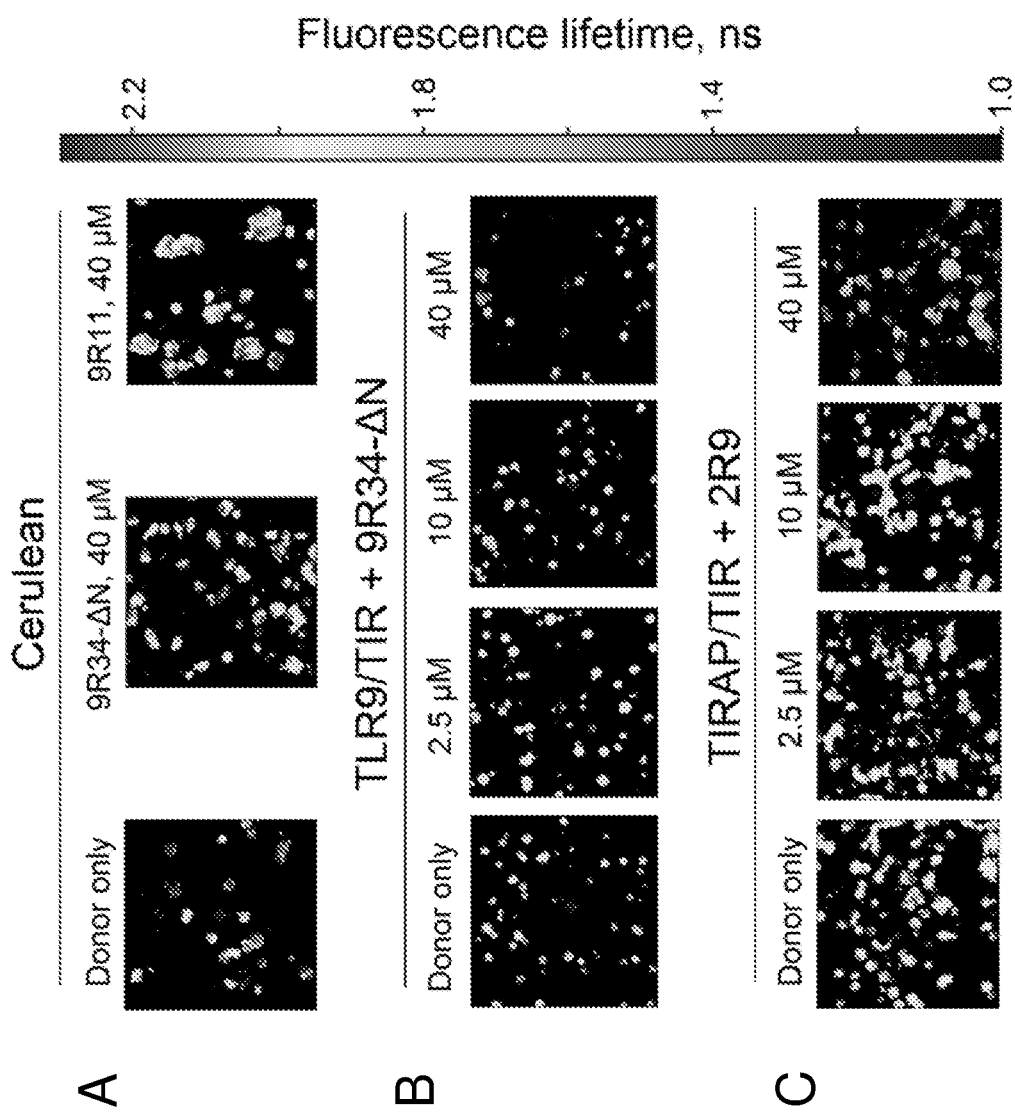
FIG. 11A, FIG. 11B and FIG. 11C are sets of FLIM images of HeLa cells transfected with Cer-TIR constructs and treated with different concentrations of Cy3-labeled peptides as indicated (Cerulean, FIG. 11A; TLR9/TIR-Cer+ 9R34-ΔN, FIG. 11B; TIRAP/TIR-Cer+2R9, FIG. 11C. The decreased fluorescence lifetime in the rightmost images of panels B and C indicates quenching of Cer fluorescence caused by direct TIR-peptide binding.

TLR9 inhibitory peptide 9R34-ΔN followed the same pattern and bound the receptor TIR domain (FIG. 11). These data collectively suggest that the position of TLR dimerization interface is conserved generally in the TLR family, with one of the TLR TIR dimerization interfaces being formed by a broad area that might include residues of AB and/or BB loops, and also β-strand B (FIG. 2A). Binding studies have suggested that 9R34-ΔN binds not only TLR9 TIR, but also TIRAP TIR (yet with apparently lower affinity), but does not interact with MyD88 TIR (see FIG. 13).

Figure 13:
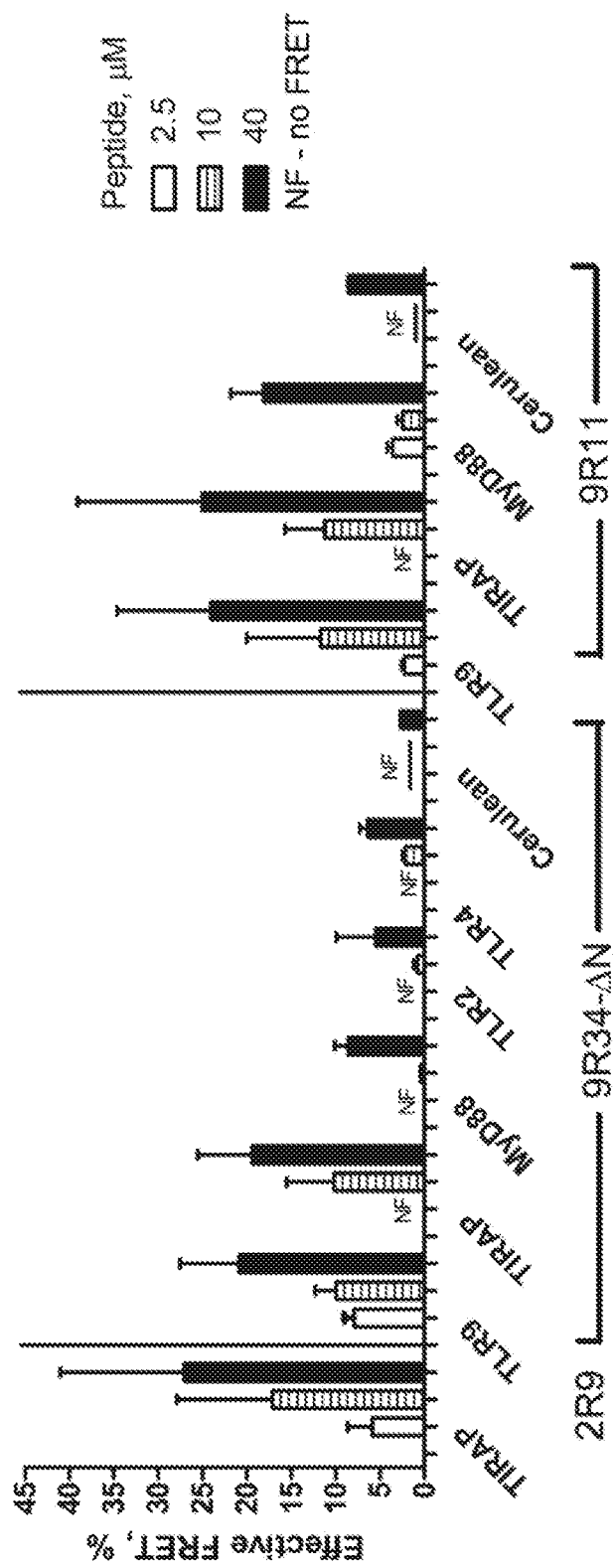
FIG. 13 is a bar graph showing FRET efficiency results for different TIR-peptide pairs.

Multispecificity of TIR-TIR interactions mediated by the BB loop has been previously reviewed. At the same time, BB loop-mediated TIR-TIR interactions are not altogether general, as demonstrated, for example, by the fact of differential adapter recruitment to activated TLRs. Inhibitory peptide 9R34-ΔN faithfully mimics this general binding property of whole length TIR domains as it binds TLR9 and TIRAP TIR domains, but not the MyD88 TIR (FIG. 13). Such a binding profile is consistent with the models of primary receptor complex in which TLR TIR dimer is formed by an asymmetric interaction in which the Surface 1 of one TIR domain mediates TLR TIR dimerization, whereas the same region of the second TLR of the dimer is available for TIRAP recruitment (see FIG. 1C).

Previously identified Region 9 TLR peptides bound preferentially the adapter TIR domains, not TLR TIRs. In addition, 4R9, a TLR4 peptide, did not bind TLR4 TIR, but co-immunoprecipitated with TIRAP. 2R9, a peptide from Region 9 of TLR2, was TIRAP-selective in a cell-based FRET assay and bound recombinant TIRAP with nanomolar affinity. Peptides from Region 9 of TLR1 and TLR6 inhibited cognate receptors and bound MyD88 and TIRAP, respectively. These findings suggest that α-helix D of TLR TIR domains is an essential part of the adapter recruitment site. The TLR9 peptide 9R9 inhibited signaling weaker than 9R34 or 9R11 (see FIG. 3 and FIG. 4). Therefore, whether this peptide also binds a TLR adapter could not be confirmed at this time. The area that corresponds to 9R9 and includes helix D and neighboring loops is shown as Surface 3 (S3) in FIG. 1.

However, it seems likely that the segment represented by 9R9 is a part of an adapter recruitment site. The weaker inhibitory activity of this peptide may result from unspecific binding to unrelated proteins, for example serum proteins, susceptibility to peptidases, or other reasons.

Figure 2:
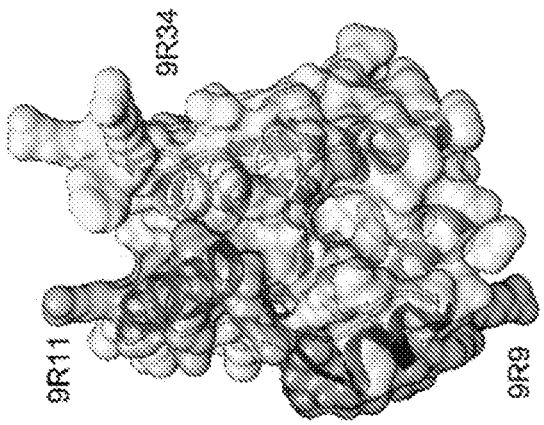
FIG. 2 shows segments of TIR domains represented by TLR9 peptides, including positions of all peptides of the primary library (FIG. 2A), and positions of inhibitory peptides 9R34, 9R9, and 9R11 (FIG. 2B).
Figure 2:
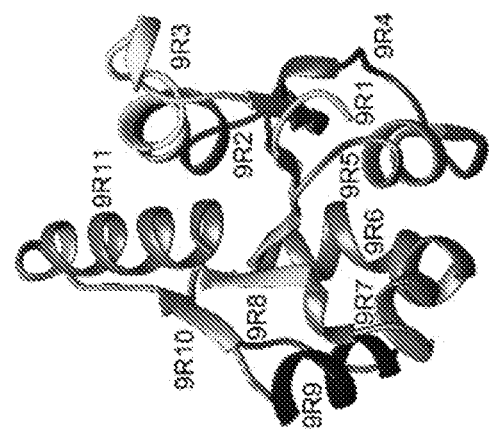

The third inhibitory peptide from the TLR9 library, 9R11, corresponds to the α-helix E (Region 11) (FIG. 2). Peptide 4α-E from α-helix E of TLR4 (SEQ ID NO:39) also inhibited cognate signaling. Peptides from α-helices E of TLR1, 2 or 6, however, did not affect TLR2 signaling; although TLR1 and TLR6 peptides from neighboring Region 10 that included DE and EE loops, and β-strand E inhibited. A cell-based binding assay has demonstrated that 4RaE binds to the TLR4 TIR.

Consistently, new data show that the structurally homologous peptide from TLR9, 9R1 1, also binds to the receptor TIR. FIG. 1 shows schematics of adapter recruitment to activated TLR9, location of TIR segments that constitute inhibitory peptides, and interaction modes the TIR domains interact in the context of TLR signaling complexes. TLR9 TIR dimers recruit adapters through intrastrand and interstrand interactions. The TLR9 TIR complex elongates bidirectionally in the presence of TIRAP and MyD88. Bidirectional elongation of TLR9 signaling protofilaments is possible due to ability of TLR9 S1 to interact with TIRAP and the ability of TLR9 S4 to bind either TIRAP or MyD88. Adapter-adapter S2-S3 interstrand interactions occur after elongation of the receptor filament through intrafilament S1-S4 interactions.

9R11, however, demonstrated a multispecific binding as this peptide also bound TIRAP and, to a lesser degree, MyD88 (FIG. 13). Thus, inhibition profiles obtained for TLR2, TLR4, and TLR9 peptide libraries collectively reveal a significant similarity and suggest a common mode of TLR TIR dimerization in which one TIR of the dimer interacts with other through Surface 1, a large area that is centered on the β-strand B and may include either BB or AB loop, or parts of both. Surface 1 appears to interact asymmetrically with the region generally located on the opposite surface of the TIR, in the vicinity of α-helix and β-strand E (Surface 4). See FIG. 1B.

The area near helix E is highly fragmented. Therefore, in addition to helix E residues, the second dimerization interface may include isolated residues from helix E neighboring regions, i.e., β-strand E, loops adjacent to the β-strand E, the N-terminal half of β-strand D, the DD loop, and also residues of the most C-terminal round of α-helix D (see FIG. 2D). Because the position of this dimerization interface slightly varies in different TIRs and is formed by not conserved amino acid sequences, this broad area is shown as Surface 1 (S1) in FIG. 2.

The model proposes that both TLR9 monomers interact with the TIR domains of adapters (either TIRAP or MyD88) via α-helix D and adjacent regions (R9). Trimer formation causes further structure elongation with TIRAP or MyD88 TIRs. Sufficient amounts of MyD88 in a filament elicit formation of myDDosome complexes and promote further TLR9 signal transduction. TIRAP cannot initiate TLR signaling itself because it lacks a death-domain. Moreover, it is determined that TLR9 signaling can proceed in the absence of TIRAP. However, in some cases, cells which lack TIRAP completely lose their ability to respond to the TLR9 stimuli. In addition, the absence of TIRAP can significantly impair the formation of myDDosome complex.

The described mechanism of interactions between TLR TIRs is in line with the model recently proposed by Ve et al., which is based on the study of oligomeric filaments spontaneously formed by TIRAP, MyD88, and a mixture of these proteins. This model suggests that filaments made only by MyD88 is more fragile than when it made by both adapter proteins. Accordingly, TLR TIR dimerization leads to the formation of the filamentous signaling complex comprised of TIR domains. Ve et al. postulated that interactions of TIR domains in the primary TLR signaling complexes resemble interactions in the double-stranded protofilaments that comprise larger TIRAP filaments. Two types of TIR-TIR interactions mediate the assembly of the double stranded TIR filaments. TIR interactions within the strands are through two regions that are located near β-strands that form two opposite edges of the central O-sheet, strands B and E (these areas remarkably well correspond to Surfaces 1 and 4 suggested by decoy peptide screenings).

Ve et al. highlighted four broad TIRAP TIR surfaces (BB, BC, CD and EE), which are capable to mediate interactions within the filamentous structure made by TIRAP molecules. Listed surfaces in general match with four peptide regions, R3/R4, R6, R9 and R11 of the TIR domain, which in many cases produce the inhibitory peptides. The difference between the models is, however, that unlike the intrastrand interactions in the multifilamentous TIRAP complex, which are predominantly mediated by the BB loop residues, interactions of other TIR domains may involve a broader region including the AB loop and residues from β-strand B. The recent report on the interactions between TIR domains of adaptor proteins suggests that TIRAP and MyD88, as well as a mixture of these proteins, can form large oligomeric open-ended structures.

Combining our results with the study published by Ve et al, a universal mechanism of initiation of intracellular TLR signaling is suggested. Two TIR surfaces, Surface 1 (S1) that approximately includes residues from AB, BB loops, and β-strand B (in case of TLR9, S1 is represented by peptide 9R34) and Surface 4 (S4) that may embrace 1-strand E, and some adjacent sequences, mutually interact to form the intra-strand bonds within TLR signaling filaments (FIG. 1). Two other surfaces, Surface 2 (S2), which can contain residues of α-helix B and/or α-helix C, and Surface 3 (S3) comprised α-helix D and contiguous sequences also mutually interact to create bonds between two filaments of the double-stranded filamentous structure of the signaling-initiating complex (FIG. 1). In the outcome of described interactions a filamentous multi-TIR structure can be created and further elongated with additional TIRs in both directions from the initial complex (FIG. 2E). Thus, according to this model, after recruiting an adapter protein dimerized TLR forms sufficient binding surface for the further filament elongation and formation of a higher-order protein complex.

Interactions of TIR domains that belong to different strands of the double-stranded TIRAP protofilament are mediated by two separate, mutually interacting surfaces (FIG. 1). One interstrand interface of TIRAP protofilaments includes residues of α-helix D and CD loop; this interface corresponds to Surface 3 (S3 in FIG. 1A). The second interstrand interface of TIRAP protofilaments is jointly formed by helices B and C. The corresponding residues of TLR9 are indicated as Surface 2 (S2) in FIG. 1A.

Importantly, interaction surfaces in the TIRAP protofilament match to the putative TIR-TIR interfaces suggested by previous studies of TIRAP-derived decoy peptides. Thus, early studies suggested that the BB loop peptide can block important TIRAP functions. Couture et al. later found additional peptides (TR3, TR5, TR6, TR9, and TR11) that inhibit TIRAP-mediated signaling and specified that signaling inhibition by TIRAP BB loop peptide critically depends on the N-terminal leucine. TIRAP-derived inhibitory peptides TR5 and TR6, first reported by Couture et al., correspond to the second interfilament interface of TIRAP protofilaments, indicated as S2 in FIG. 1. Peptide TR9 represented Surface 3, whereas TR11 and TR3 respectively corresponded to S4 and S1.

Thus, screening of TLR9-derived peptides reveals significant topological similarity of positions of new inhibitory peptides with that in previously screened peptide libraries. Moreover, the inhibitory peptides come from regions that are structurally homologous to TIR-TIR interfaces in the TIRAP protofilaments. These findings together support the hypothesis of structural similarity of receptor and adapter TIR interactions in the signal-initiating complexes; yet, particular TIRs of the complex may interact through slightly different structural regions. Particularly, our data suggest that the AB loop of TLRs play more important role in TIR-TIR recognition than the BB loop. The finding that TIR-TIR interface positions are structurally conserved is remarkable considering sequence dissimilarity of corresponding segments. An example of sequence dissimilarity of corresponding interface regions are sequences of TIRAP, TLR4, TLR2, and TLR9 inhibitory peptides from Region 9 and 11 (TR9a: AAYPPELRFMYYVD, SEQ ID NO:34; 4R9: LRQQVELYRLLSR, SEQ ID NO:37; 2R9: PQRFCKLRKIMNT, SEQ ID NO:38; TR11a: GGFYQVKEAVIHY, SEQ ID NO:36; 4αE: HIFWRRLKNALLD; SEQ ID NO:39; 9R11: RSFWAQLGMALTRD, SEQ ID NO:24).

The surfaces that mediate TIR-TIR interactions are highlighted in FIG. 1A. Surfaces 1-4. In TLR9, Surfaces 1 and 4 correspond to peptides 9R34 and 9R11. These surfaces mediate dimerization of TLR TIRs and also adapter recruitment through lateral intrafilament interactions. Surfaces 2 and 3 in TLR9 correspond to peptides 9R6 and 9R9 (9R6 exhibited partial activity in respect to TNFα and IL-12-p40 mRNA (FIG. 3). These Surfaces recruit adapter TIRs that initiate the formation of the second strand of the primary TIR complex (FIG. 1B). The second strand stabilizes the complex and provides sufficient number of MyD88 molecules to initiate myDDosome formation.

Experimental data support this model of TIR domain interactions in several ways. One prediction from the filamentous, double-stranded structure of the signaling-initiating TIR complex is that both surfaces that mediate TLR TIR dimerization may be responsible for adapter recruitment through the intrastrand interactions (FIG. 1B and FIG. 1C). Our data confirm this prediction because both inhibitory peptides that correspond to two separate TLR9 dimerization interfaces, 9R34-ΔN and 9R11, demonstrate multispecific binding. Peptide 9R34-ΔN, from S1, binds TLR9 and TIRAP TIR domains, not MyD88, whereas 9R11 (this peptide represents S4) interacts with all relevant TIR domains (FIG. 13).

Figure 12:
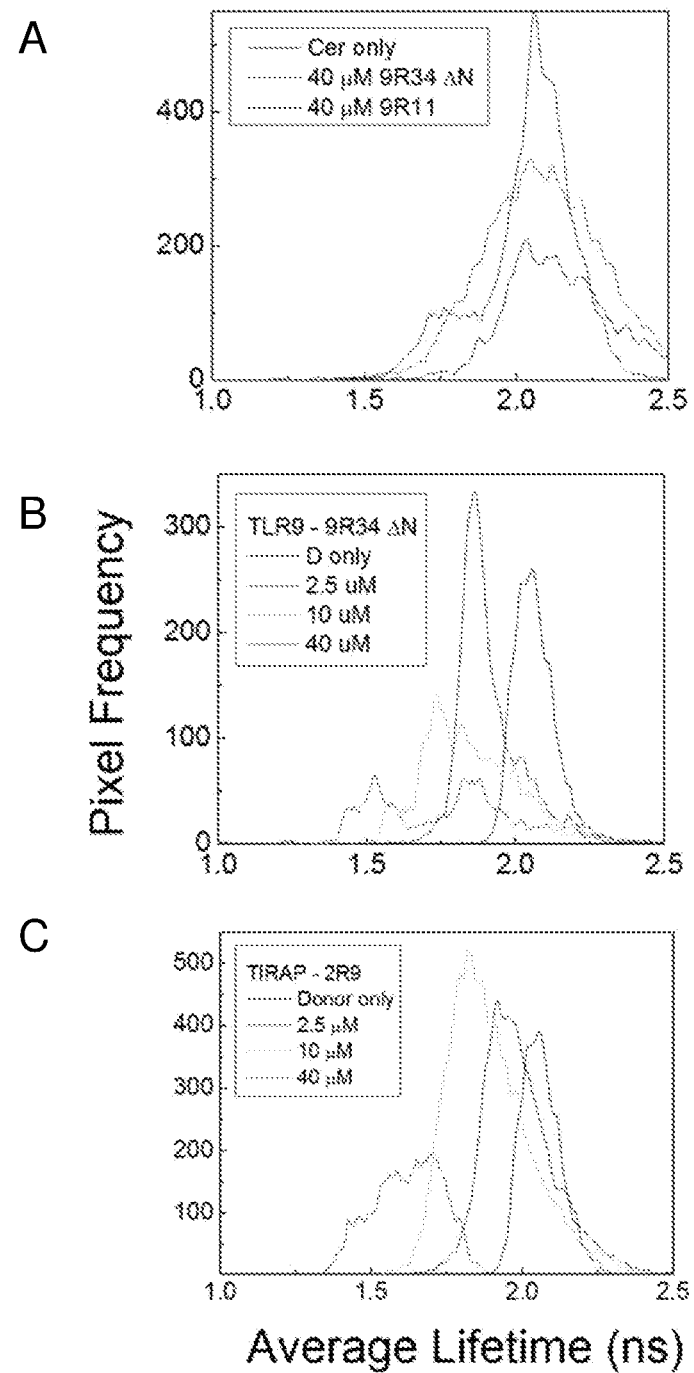
FIG. 12A, FIG. 12B, and FIG. 12C are histograms showing the frequencies of occurrence of particular average lifetimes in the images shown in FIG. 11.

Another consequence from the adapter recruitment model suggested by TIRAP filament structure and decoy peptide screenings is that adapters are independently recruited to filament ends through different surfaces of the receptor dimer that may have different binding specificities. This, in turn, implies that the initial receptor complex can elongate from either or both ends (FIG. 1C, FIG. 1D, FIG. 1E, and FIG. 1F). In the case of TLR9, peptide from Surface 1 binds TIRAP, not MyD88; whereas the peptide from opposite Surface 4 can bind either TIRAP or MyD88 (FIG. 11, FIG. 12, and FIG. 13). Such binding preferences suggest that the initial complex can elongate bidirectionally in the presence of TIRAP and MyD88 (FIG. 1C). In the absence of TIRAP, the TLR9 complex can elongate only in one direction, through MyD88 recruitment only to Surface 4 of the TLR9 TIR dimer (FIG. 1D). Such models reconcile previous discussions on the role of TIRAP in TLR9 signaling. While early studies concluded that TIRAP is not required for TLR9 signaling, it was later discovered that TLR9 responses to certain viruses are critically diminished in TIRAP absence and the TIRAP-targeting peptide strongly suppresses TLR9 signaling in wild-type cells. The TIRAP-dependent bidirectional elongation of protosignalosomes explains both the ability of TLR9 to signal in TIRAP-deficient models and the sensitivity of TLR9 responses to TIRAP targeting in wild type cells.

Latty et al. recently applied single-molecule fluorescence microscopy to study formation of myDDosomes in response to TLR4 stimulation. Intriguingly, authors observed that a large LPS dose caused formation of "super myDDosomes," the signaling complexes that are comprised of twice as many MyD88 molecules as regular myDDosomes. These observations support the possibility of bidirectional protofilament elongation that may cause formation of two myDDosomes per one TLR4 dimer simultaneously, analogously to the schematic shown in FIG. 1C for TLR9.

Previous studies had demonstrated that peptide derived from Surface 1 of TLR2, 2R3, inhibits TLR2/1 and TLR2/6 signaling and binds both TLR2 co-receptors, whereas peptides from Surface 1 of TLR1 or TLR6 do not inhibit. We also found that Surface 3 peptides from TLR1, TLR2, and TLR6 inhibit corresponding signaling and bind MyD88 or TIRAP. These findings suggest that primary TLR2 complexes elongate in the unidirectional mode, as schematically shown in FIG. 1E and FIG. 1F.

In summary, this invention identifies TLR9-derived inhibitory peptides that block TLR9 signaling in vitro and in vivo and suggest a common mode of TIR domain interactions in the primary receptor complex that mediate adapter recruitment and thereby initiate intracellular TLR signaling. Interacting in that mode, TIR domains form a double-stranded, parallel structure that can elongate from one or both ends. Interactions within each filament are mediated by regions located near β-strands that form the edges of TIR 0-sheet; whereas interfilament interactions are through two sites, one of which is predominantly formed by helix D and another combines residues of helices B and C.

In the case of TLR9, the following model for signal initiation can be hypothesized (see FIG. 1B and FIG. 1C). TIR dimerization and trimerization steps are decisive for the assembly of the filament, whereas further its extension passes more easily and fast. Upon receptor dimerization, two TIR domains come into the close proximity. TLR9 monomers dimerize and form an inner-strand bond through the interaction between Surface 11 of the first receptor's monomer (TLR9) and the opposite Surface 1 of the second monomer (TLR9) (see FIG. 1A and FIG. 1B).

Then, TLR9 dimer, through Surfaces 2 and 3, recruits the adapter proteins (either TIRAP or MyD88) creating outer-strand bonds (see FIG. 1B). The formation of initial TIR complex causes further elongation of filamentous structure with TIRAP and/or MyD88 TIR domains (FIG. 1C). The most probable sites of this interaction are the surface formed by AB loop, β-strand B, and BB loop (S1) and a surface constituted by α-helix E and adjacent regions (S2) (see FIG. 1, which shows interacting Surfaces and schematics for adapter recruitment to activated TLRs).

Based on the data provided by Ve et al. and the data presented here in FIG. 13, MyD88, through its S1 can be seen to also interact with S4 of TLR9 (FIG. 1C and FIG. 1D). On the other hand, the present peptide binding studies showed that MyD88 did not interact with the opposite Surface 1 of TLR9 (see FIG. 13 and FIG. 1D). The subsequent filament extension with the adapter proteins is mediated by the intra-strand S1-S4 interactions and inter-strand S2-S3 interactions between TIR domains. On the contrary with MyD88, TIRAP's ability to bind 9R34 of TLR9 (FIG. 13) apparently can enable bidirectional elongation of the signaling filament from the central TLR9 dimer in the presence of both TIRAP and MyD88 (see FIG. 1C). Such an assumption can explain more robust TLR9 signaling in the presence of TIRAP. According to the present results, discusses in detail below, we assume that MyD88-only TLR9 signaling filament produces less signaling, because MyD88 can bind only S4 region of TLR9 (see FIG. 1D). Thus, such filament can be elongated only in one direction (FIG. 1D). On the contrary, binding S4 of TLR9 (1), S1 of TLR9 (2) or both of them, TIRAP makes all the structure more stable and facilitates filament extension in both directions (FIG. 1B and FIG. 1C). It can explain more robust TLR9 signaling in the presence of TIRAP.

Several studies have demonstrated that TLR9 signaling can proceed in the absence of TIRAP either, yet less effective. Bonham et al. demonstrated that the absence of TIRAP can significantly impair the formation of myDDosome. In addition, authors showed that in some cases, cells which lack TIRAP lose their ability to respond to the TLR9 stimuli. These observations are in agreement with the Ve et al. study, which revealed that filaments made only by MyD88 are more fragile than when they are made by both adapter proteins. In the absence of TIRAP, MyD88 molecules should be able to initially bind Surfaces 2 and 3 of both TLR9 monomers. But further formation of signaling filament with MyD88 can proceed only in one direction from the TLR9 dimer, because of inability of MyD88 to bind S1 of TLR9 (see FIG. 1D).

Also, in a similar way the mechanisms for initiation of TLR1/2 and TLR2/6 signaling can be described. Initially, TLR2 TIR dimerizes with either TLR1 or TLR6 through its Surface 1 (see FIG. 1). Both TLR1 and TLR6 TIRs interact with TLR2 via Surface 4. Upon receptors dimerization, Surfaces 2 and 3 of TLRs recruit adapter proteins (see FIG. 1). Data have demonstrated that TLR2 and TLR6 co-immunoprecipitated with TIRAP, whereas TLR1 with MyD88 (see FIG. 1B, FIG. 1C, FIG. 1D, FIG. 1E and FIG. 1F). Initially formed receptor-adapter complexes create a sufficient scaffold for the further elongation of the signaling filament. Studies have not revealed any TIRAP or MyD88 binding sites on Surface 1 of TLR1 or TLR6. Thus, one can assume that additional adapter protein molecules can extend filament in one direction from TLR dimer through the intra- and inter-strand interactions with TLR2 and TIRAP previously attached to the receptor heterodimers through S3 of TLR2 TIR (see FIG. 1E and FIG. 1F).

In summary, this study identifies TLR9-derived inhibitory peptides, which effectively block TLR9 signaling in vitro and in vivo. Moreover, the findings suggest a common mode of TIR domain interactions that mediate TLR dimerization and adapter recruitment initiating intracellular TLR signaling.

The TIR domain peptides that make up the TIR-derived decoy peptides (not fused to the antennapedia homeodomain cell-permeating peptide or fused to other cell-permeating moiety) are encompassed within the scope of the invention. These TIR domain peptides may be utilized in the same manner as the decoy peptides, where the assistance of a cell permeability factor is not required or is provided by other means. The present invention includes the TIR domain peptides SEQ ID NOs:4, 6, 8, 10, 12, 21, and 24, based on TLR9.

The TIR-derived decoy peptides of the present invention include those based on segments of TLR9, for example SEQ ID NOs:5, 7, 9, 11, 13, 22, and 25, also based on TLR9, but also containing a cell-permeating peptide vector. Preferably, these TIR-derived decoy peptides comprise (i) the antennapedia cell-permeating peptide (RQIKIWFQNRRMKWKK; SEQ ID NO:1) fused to (ii) segments of the TLR9 TIR domain. These decoy peptides are set forth in Table 1. In particular, these TIR-derived decoy peptides generally target the TLR9 signaling pathway.

Variants of the TIR and decoy peptides are contemplated as part of the invention as well. The variants of the present invention are based on the TIR-derived decoy peptides and the TIR domain peptides provided herein. The variants have similar or the same activity as the decoy peptides and the domain peptides, and have one or two amino acid changes from the original sequence, individually selected from additions, substitutions and deletions, based on the amino acid sequence of the unaltered version of the peptide.

The one or two changes in amino acid can be in the portion of the peptide corresponding to a TIR domain, or the portion of the peptide corresponding to the cell-permeating peptide, or both. When amino acid substitutions are made, the substitutions can be conservative or non-conservative substitutions. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Mutations can also be introduced randomly along all or part of a peptide of the invention, such as by saturation mutagenesis, and the resultant variants can be screened for activity.

The TIR-derived decoy peptides and the TIR domain peptides, and the variants thereof, of the present invention may be used in a number of different applications, primarily related to blocking or inhibiting TLR signaling. Because TLR signaling requires interaction between more than two TIR domain-containing proteins, such as dimerization of two TLRs, recruitment of several TIR domain-containing adapter proteins to activated TLRs, and interaction of two or more TIR domain-containing adapter proteins, interruption of TIR:TIR interactions can block or inhibit many different aspects of TLR signaling pathways. Therefore, the present invention includes methods of inhibiting TIR:TIR interaction between two TIR domain-bearing proteins comprising contacting a cell expressing TIR domain-bearing proteins with an effective amount of one or more of the TIR-derived decoy peptides and the TIR domain peptides, or variants thereof, of the present invention. In a particular aspect, the invention is drawn to methods of inhibiting TIR:TIR interaction between two TIR domain-bearing proteins comprising contacting a cell expressing TIR domain-bearing proteins with an effective amount of one or more of the TIR-derived decoy peptides, or variants thereof.

The TIR domain-bearing proteins are TLRs, or TLR adapter proteins, or both. The TLRs may be any TLR, for example, but not limited to, one or more receptors selected from the group consisting of TLR1, TLR2, TLR3, TLR4, TLR5, TLR6, TLR7, TLR8, TLR9, TLR10, TLR11, TLR12, and TLR13. In one aspect, the TLR is TLR2 or TLR4, or TLR9. The TLR adapter protein may be any TLR adapter protein, for example, but not limited to, one or more proteins selected from the group consisting of TIRAP, MyD88, TRIF, and TRAM. The one or more TIR-derived decoy peptides and the one or more TIR domain peptides are those provided in Table 1. In one example, the TIR-derived decoy peptides are one or more selected from the group consisting of 9R34 and its N- and C-terminal deletion modifications, 9R34-C/S, 9R9 and 9R11, preferably 9R34 and modifications thereof.

The invention also includes methods of inhibiting TLR activation comprising contacting a cell expressing TLRs with an effective amount of one or more of the TIR-derived decoy peptides and the TIR domain peptides, or variants thereof, of the present invention. In a particular aspect, the invention is drawn to methods of inhibiting TLR activation comprising contacting a cell expressing TLRs with an effective amount of one or more of the TIR-derived decoy peptides, or variants thereof.

The TLRs may be any TLR, for example, but not limited, one or more receptors selected from the group consisting of TLR1, TLR2, TLR3, TLR4, TLR5, TLR6, TLR7, TLR8, TLR9, TLR10, TLR11, TLR12, and TLR13. In one aspect, the TLR is TLR2 or TLR4, or TLR9. The one or more TIR-derived decoy peptides and the one or more TIR domain peptides are those provided in Table 1. In one example, the TIR-derived domain and decoy peptides are one or more based on TR3, TR5, TR6, TR9 and/or TR11, preferably based on TR9. Domain peptides contemplated as part of the present invention include SEQ ID NOs:4, 6, 8, 10, 12, 21, and 24, which optionally also include a cell-permeating peptide vector at the N- or C-terminus, such as SEQ ID NOs:5, 7, 8, 11, 13, 22, and 25, which are termed decoy peptides and contain the preferred cell permeating peptide vector from antennapedia.

The invention further includes methods of inhibiting TLR-mediated signaling comprising contacting a cell expressing TLRs with an effective amount of one or more of the TIR-derived decoy peptides and the TIR domain peptides, or variants thereof, of the present invention. In a particular aspect, the invention is drawn to methods of inhibiting TLR-mediated signaling comprising contacting a cell expressing TLRs with an effective amount of one or more of the TIR-derived decoy peptides, or variants thereof.

Additional methods are contemplated as part of the invention. Such methods include contacting a cell with any of the peptides disclosed herein in vitro, such as in a laboratory experiment, including a screening assay; or with a subject in vivo or ex vivo, such as a method for treating a disease or condition in the subject.

The effective amount of decoy peptides, domain peptides and variants thereof used in the in vitro methods described herein will vary depending on a cell type and experimental conditions when the cell is contacted. However, in general, an effective amount is between about 0.5 µM and 100 µM, and includes between about 0.5 µM and 100 µM, between about 1 µM and 75 µM, between about 5 µM and 50 µM, between about 20 µM and 40 µM and includes about 0.5 µM, 1 µM, 5 µM, 10 µM, 15 µM, 20 µM, 25 µM, 30 µM, 35 µM, 40 PM, 45 µM, 50 µM, 55 µM, and 60 µM.

A preparation comprising one or more of the decoy peptides, domain peptides and variants thereof may be prepared by adding the peptides to PBS (phosphate-buffered saline) or cell culture medium or any suitable pharmaceutical excipient or group of excipients.

The TIR-derived decoy peptides and the TIR domain peptides, and the variants thereof, of the present invention may also be used in methods of treating diseases and conditions in subjects suffering from or afflicted with a condition exacerbated by TLR signaling. For example, the invention is drawn to methods of treating a subject having a condition mediated by TLR signaling comprising administering to a subject in need thereof a therapeutically-effective amount of a pharmaceutical composition comprising one or more of the TIR-derived decoy peptides and the TIR domain peptides, and variants thereof, of the present invention and a pharmaceutically acceptable excipient or group of excipients, such as a carrier or diluent. The invention also includes such pharmaceutical compositions.

In a particular aspect, the invention is drawn to methods of treating a subject having a condition mediated by TLR signaling comprising administering to a subject in need thereof a therapeutically-effective amount of a pharmaceutical composition comprising one or more of the TIR-derived decoy peptides, and variants thereof, and a pharmaceutically acceptable excipient or group of excipients. The one or more TIR-derived decoy peptides and TIR domain peptides are those described herein.

The condition mediated by TLR signaling may be any condition where dysregulation of a TLR signaling pathway results in a disease or condition in a subject that might be cured, improved, lessened, etc. by inhibiting or blocking TLR signaling in the subject. Such conditions include, but are not limited to, inflammation, generalized infection or sepsis, septic shock, autoimmune disease, or an inflammatory or genetic disease promoted by TLR activation which exacerbates or causes the disease. In particular, the following diseases and conditions also are contemplated for methods using the peptides of the invention: systemic lupus erythematosis, multiple sclerosis, plaque psoriasis, rheumatoid arthritis, graft versus host disease, arthritis, Sjogren's syndrome, cancer, viral infection, transplant rejection, and reactions to antimalarials and/or antipsoriatics.

The invention is also drawn to methods of treating a subject in need, having any one or more of the conditions listed above comprising administering to the subject a therapeutically-effective amount of a pharmaceutical composition comprising one or more of the TIR-derived decoy peptides and/or the TIR domain peptides, and variants thereof, of the present invention (see Table 1), optionally with a pharmaceutically acceptable excipient, carrier or diluent. The one or more TIR-derived decoy peptides and TIR domain peptides are those described herein.

The peptides of the present invention can be formulated in a pharmaceutical composition that is suitable for administration to a subject. The pharmaceutical compositions comprise one or more of the peptides and optionally a pharmaceutically acceptable diluent, carrier, and/or excipient, such as one or more of a sterile water or saline for injection, PBS, buffer, a surfactant, a dispersing agent, a preservative, a solubilizing agent, an isotonicity agent, or any other pharmacologically inert vehicle for delivering the peptides of the invention to a subject. Conventional techniques for preparing pharmaceutical compositions are disclosed, for example in: Remington, The Science and Practice of Pharmacy, 19th ed., Gennaro, Ed., Mack Publishing Co., Easton, Pa. 1995.

The pharmaceutical compositions of the present invention may be formulated, for example, for oral, sublingual, intranasal, intraocular, rectal, transdermal, mucosal, pulmonary, topical or parenteral administration. Parenteral modes of administration include without limitation, intradermal, subcutaneous, intramuscular, intravenous, intraperitoneal, intraarterial, intramedullary, intracardiac, intra-articular, intrasynovial, intracranial, intraspinal, and intrathecal. Any known device useful for parenteral injection or infusion of pharmaceutical formulations can be used to effect such administration.

Depending on the means of administration, the dosage may be administered all at once, such as with an oral formulation in a capsule or liquid, or slowly over a period of time, such as with an intramuscular or intravenous administration, or in periodic doses over a period of minutes, hours, days, weeks, or months.

The therapeutically-effective amount of peptide will vary depending upon the physical characteristics of the subject, the severity of the subject's symptoms, the particular disease or condition being treated, the formulation and the means used to administer the peptides, the number of doses being administered to the subject over the course of treatment, and the method being practiced. The specific dose for a given subject is usually set by the judgment of the attending physician. However, it is considered that the effective amount of decoy peptides, domain peptides and variants thereof used in the methods of treatment described herein will generally be between about 0.1 nmol/g and 50 nmol/g, and includes between about 1 nmol/g and 50 nmol/g, between about 1 nmol/g and 30 nmol/g, between about 5 nmol/g and 40 nmol/g, and between about 5 nmol/g and 25 nmol/g. Suitable values also include about 0.5 nmol/g, 2 nmol/g, 4 nmol/g, 6 nmol/g, 8 nmol/g, 10 nmol/g, 12 nmol/g, 14 nmol/g, 16 nmol/g, 18 nmol/g, 20 nmol/g, 22 nmol/g, 24 nmol/g, and 26 nmol/g.

Administration frequencies for the pharmaceutical compositions of the present invention include 4, 3, 2 or once daily, every other day, every third day, every fourth day, every fifth day, every sixth day, once weekly, every eight days, every nine days, every ten days, bi-weekly, monthly and bi-monthly. The duration of treatment will be based on the condition being treated and will be best determined by the attending physician. However, continuation of treatment is contemplated to last for a number of days, weeks, or months.

In each of these embodiments, the subject is a bird or mammal, including zoo and farm animals, game animals, laboratory animals, companion and service animals, primates and humans, which include but are not limited to humans, non-human primates, chickens, geese, ducks, horses, cows, goats, sheep, dogs, cats, rabbits, and rodents.

3. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims.

Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

Example 1: General Methods

1. Animals and Cells

Eight week old female C57BL/6J mice were obtained from the Jackson Laboratorym (Bar Harbor, Maine). Bone marrow-derived macrophages (BMDM) were isolated and cultivated according to known methods (see Weischenfeldt and Porse, 2008). Mouse tibias and femurs were flushed with the ice-cold PBS and the cells obtained transferred to RPMI 1640 supplemented with 10% L929 cell supernatant. The cells were cultured for 10-14 days prior to experiments.

2. TLR Agonists

ODN 1668, S-(2,3-bis (palmitoyloxy)-(2R, 2S)-propyl)-N-palmitoyl-(R)-Cys-Ser-Lys4-OH (Pam3C), and R848 were purchased from InvivoGenr (San Diego, CA). Phenol purified, *Escherichia coli* K235 LPS (65) was a kind gift of Dr. Stefanie N. Vogel (UMB SOM).

3. Peptide Design, Synthesis, and Reconstitution

TLR9 sequence TIR domain fragments were synthesized in tandem with the cell-permeating antennapedia homeodomain sequence (RQIKIWFQNRRMKWKK; SEQ ID NO:1), placed at the N-terminus. This vector is effective for intracellular delivery of inhibitory decoy sequences in vitro and in vivo. Peptide sequences are shown in Table 1.

CPDP were synthesized by Aapptec™ (Louisville, KY) or GenScript™ (Piscataway, NJ). The Cy3-labeled peptides were produced by CPC Scientific™ Inc., (Sunnyvale, CA) and Lifetein™ (Franklin Township, NJ). The Cy3 label was placed at the peptide N-terminus. The purity of all CPDP was >95%. Concentrations of reconstituted peptides were determined spectrophotometrically. CPDP were synthesized with the cell-permeating, 16-amino-acid-long fragment of antennapedia homeodomain.

4. Evaluation of Cytokine Expression by Quantitative Real Time PCR

Two million BMDMs per well were plated in 12-well plates, incubated overnight, and treated with CPDP for 30 minutes prior to stimulation with a TLR agonist for 1 hour.

cDNA was synthesized from 1 μg of total RNA isolated using Trizo™ (Life Technologies; Carlsbad, CA) and reverse transcribed using a RevertAidr RT Reverse Transcription Kit (ThermoFisher Scientific™). The cDNA obtained was amplified with gene-specific primers for mouse HPRT, TNFα, IL-10, IL-12-p40, or IL-6 and Fast SYBR Green™ master mix (Applied Biosystemsm) as previously described.

5. ELISA Evaluation of Cytokine Secretion

One million BMDMs per well were plated in 24-well plates and treated with CPDP for 30 minutes prior to stimulation with a TLR agonist for 5 hours. Mouse TNFα and IL-12-p40 concentrations were measured in supernatants using ELISA kits from Biolegend™, Inc.

6. Immunoprecipitation of MyD88-Containing Signaling Complexes and Immunoblotting Four million BMDMs per well were plated in 6-well plates and treated with CPDP for 30 minutes prior to stimulation with ODN 1668 for 90 minutes. Cells were lysed in 600 p L of buffer containing 20 mM HEPES (pH 7.4), 150 mM NaCl, 10 mM NaF, 2 mM $Na_3VO_4$, 1 mM EDTA, 1 mM EGTA, 0.5% Triton X-100, 0.1 mM DTT, and protease inhibitor cocktail (Roche™). Cell extracts were incubated overnight with 1 μg of anti-mouse MyD88 antibody (AF3109) (R&D Systems™, followed by a 4-hour incubation with 20 μL protein G Sepharose beads (ThermoFisherm Scientific). The beads were then washed 3 times with 500 μL of lysis buffer and boiled in 60 μL of Laemmli sample buffer (Bio-Rad™). Cell extracts were electrophoresed on 10% acrylamide gel by SDS-PAGE and transferred to PVDF membrane (Bio-Rad™). Rabbit anti-MyD88 IgG was purchased from Cell Signaling™. Mouse anti-IRAK4 IgG was obtained from Abcam™. Alkaline phosphatase-conjugated secondary antibodies against mouse and rabbit IgG were purchased from Cell Signaling™. The stabilized substrate for alkaline phosphatase was from Promega™.

7. Expression Vectors

MyD88-Cer, TIRAP-Cer, and TLR2-Cer expression vectors have been described previously. Because of low expression levels, full-length TLR4-Cer and TLR9-Cer vectors were replaced with TLR4 TIR-Cer and TLR9 TIR-Cer, respectively. These vectors do not include TLR4 and TLR9 ectodomains but encode full transmembrane sections and TIR domains.

8. Fluorescence Lifetime Imaging (FLIM)

Three million HeLa cells were transfected with 10 μg of MyD88-Cer, TIRAP-Cer, TRAM-Cer, TLR2-Cer, TLR4 TIR-Cer, or TLR9 TIR-Cer expression vectors using a Lipofectamine™ 3000 kit from Invitrogen™ per manufacturer recommendations. Twenty four hours later, the transfected cells were trypsinized and reseeded into a 50-well gasket (Grace Bio-Labs™) mounted on a microscope slide at the density 8000 cells/well. The next day, cells were treated with Cy3-9R34-ΔN or Cy3-9R11 for 1 hour and fixed on the slides with a 4% paraformaldehyde solution.

Fluorescence lifetime images were acquired using the Alba V FLIM™ system (ISS™ Inc.). The excitation was from the laser diode 443 nm coupled with scanning module (ISS™) through multiband dichroic filter 443/532/635 nm (Semrock™) to Olympus™ IX71S microscope with objective 20×0.45 NA (UPlan™ Olympus™). Emission was observed through bandpass filter 480430 nm (Chroma Technology™) and detected by a photomultiplier H7422-40 (Hamamatsu™). Measurements were performed using frequency domain (FD) and time domain (TD) modalities of the FLIM system. FD FLIM data were acquired using ISS™ A320 FastFLIM™ electronics with n harmonics of 20 MHz laser repetition frequency (n=1, 2, 3, 4, 5, 6). FastFLIM™ was calibrated using fluorescein in buffer pH 8.0 as a standard with a single lifetime of 4.0 ns. TD FLIM images were acquired using time-correlated single photon counting TCSPC™ Model SPC-830 (Becker & Hick™).

Images (256×256 pixels) were acquired with resolution varied in the range ~0.4-0.7 μm/pixel, using scan speed 1 ms/pixel. To avoid pixel intensity saturation in bright cells and to improve the signal from dim cells, two to five overlapping scans were used for acquisition of FLIM images. Image sizes varied from 100×100 to 180×180 μm to accommodate multiple cells. FLIM data were analyzed with VistaVision™ Suite software (Vista™ v.212 from ISST). Fluorescence lifetime was determined using single- and bi-exponential intensity decay models. Average lifetime images were generated based on pixel-by-pixel analysis using the combined signal of two neighboring pixels in all directions (bin 2=25 pixels). The binning was used to improve the signal for analysis. The average lifetimes were calculated from fitted parameters, decay times $\tau_i$ and amplitudes $\alpha_i$, $\tau_a = \Sigma \alpha_i \tau_i$. The bi-exponential fitting procedure was performed with one lifetime component fixed at 3.1 nsec, which was found common for most images. To calculate the effective FRET efficiency (E), average lifetimes of the donor only images ($\tau_D$) and donor-acceptor images ($\tau_{DA}$) were used, $E=1-\tau_{DA}/\tau_D$. It should be noted that non-quenched donor molecules also contribute to the value of $\tau_{DA}$, more significantly at low acceptor concentrations as was discussed previously.

9. Animal Experiments

Systemic cytokine levels were measured in plasma samples obtained 1, 3, and 5 hours after intraperitoneal (i.p.) administration of 7.86 nmol (50 μg) of ODN 1668 or 67 nmol of Pam3C per mouse, using ELISA kits from Biolegend™ Inc. CPDP were dissolved in PBS and administered i.p. at the dose of 200 nmol per mouse 1 hour before administration of a TLR agonist. For survival experiments, mice were sensitized to TLR9 agonists by i.p. injection of 20 mg of D-Gal 30 minutes before administration of peptides or PBS. ODN 1668 was used at the doses of 3.93 or 7.86 nmol/mouse (25 or 50 μg/mouse) 1.5 hours after D-Gal. Animal survival was monitored for 50 hours. All agents were administered i.p. in 500 μL volume of PBS. Animals had free access to food and water during the observation period. All animal experiments were conducted in accordance with the national guidelines for the care and use of laboratory animals under a protocol that was approved by the UMB IACUC.

10. TLR9 TIR Domain Modeling

Template search was performed using BLAST (Basic Local Alignment Search Tool), HMM-HMM—based lightningfast iterative sequence search (HHBlits) and the SWISS-MODEL template library (SMTL). The target sequence was searched with BLAST against the primary amino acid sequence contained in SMTL. An initial HHblits profile has been built using the procedure outlined in, followed by 1 iteration of HHblits against NR20. The model was built based on the target-template alignment using ProMod3. All images were produced using the UCSF Chimera viewer.

11. Data Representation

Numerical data were statistically analyzed by the one way ANOVA using GraphPad™ Prism 5 software.

Figure 4:
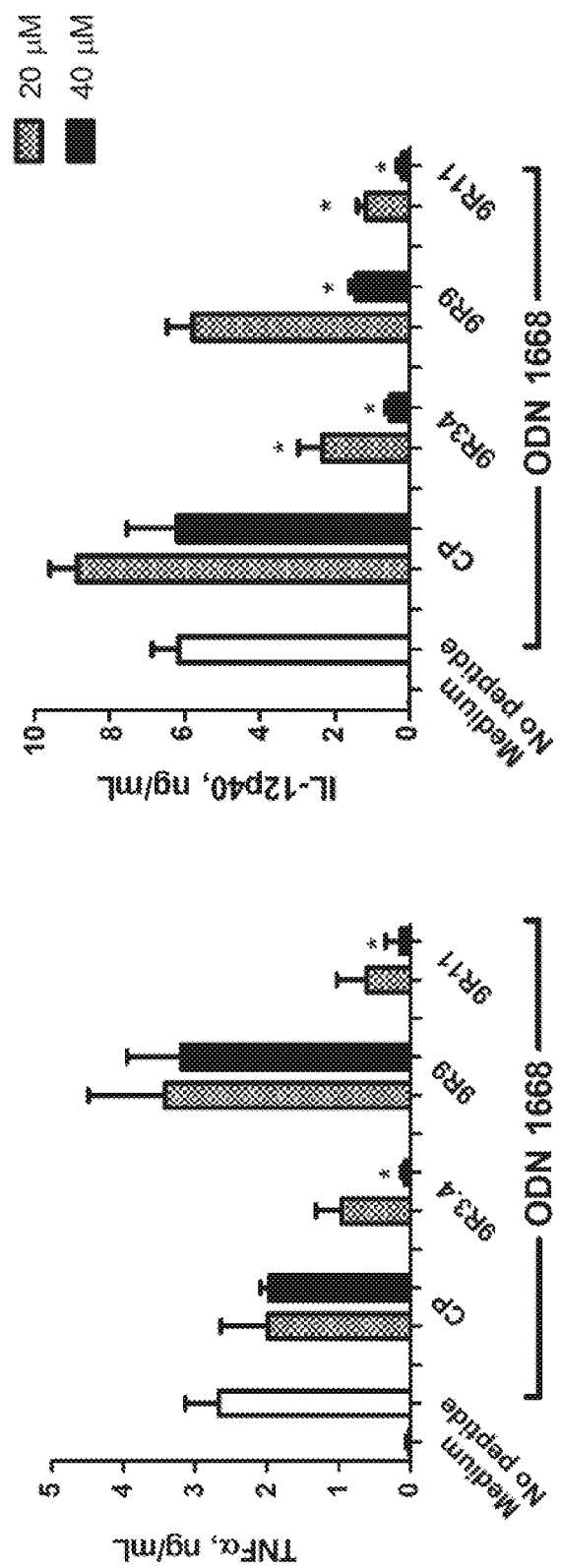
FIG. 4A and FIG. 4B are bar graphs that show TNFα and IL-12-p40 concentrations respectively, in supernatants evaluated by ELISA 5 hours after cell stimulation with ODN1668.

Example 2. Effects of TLR9-Derived CPDP on ODN 1668-Induced Cytokine Expression and Secretion In order to investigate and identify TLR9-derived cell-permeable decoy peptides (CPDP) that inhibit TLR9 signaling, the following studies were done. Mouse BMDMs were incubated in the presence of a 10, 20 or 40 μM decoy peptide for 30 minutes prior to stimulation with ODN 1668 (1 μM). FIG. 4 shows cytokine mRNA expression measured 1 hour after ODN 1668 challenge and normalized to the expression of hypoxanthine phosphoribosyltransferase (HPRT). Peptides 9R3, 9R34, 9R9, and 9R11 significantly suppressed TNFα, IL-10, and IL-12-p40 mRNA expression measured 1 hour after stimulation, whereas effect on IL-6 mRNA expression was statistically significant only for 9R34. Peptides 9R6 and 9R8 also demonstrated some inhibitory activity, but were overall less potent. Data represent the means±SEM of at least three independent experiments. The statistical significance of changes in cytokine mRNA was determined by a one-way ANOVA test; *p<0.001. Peptides 9R3 and 9R34 have overlapping sequences (see Table 1). 9R34 inhibited expression of all tested cytokines when used at lower concentrations of 10 or 20 μM (see FIG. 3).

FIG. 4 shows cytokine concentrations in supernatants, evaluated by ELISA 5 hours after cell stimulation. BMDMs were incubated in the presence of a decoy peptide for 30 minutes prior to stimulation with ODN 1668 (1 μM). The statistical significance of changes in cytokine levels was determined by the one-way ANOVA test; *p<0.01. Results show the effects of TLR9-derived cell-permeable decoy peptides on ODN 1668-induced cytokine secretion. Three most potent inhibitory peptides identified in mRNA screens, 9R34, 9R9, and 9R11, were examined further based on their effect on cytokine secretion assessed in 5 hour supernatants of ODN-stimulated BMDM. CPDPs 9R34, 9R9, and 9R11 reduced secretion of IL-12-p40 when used at 40 μM; CPDPs 9R34 and 9R11 were also effective at 20 μM (see FIG. 4). Both peptides also decreased the production of TNFα, when used at 40 PM. CPDP 9R9 did not inhibit significantly the secretion of TNFα.

Figure 5:
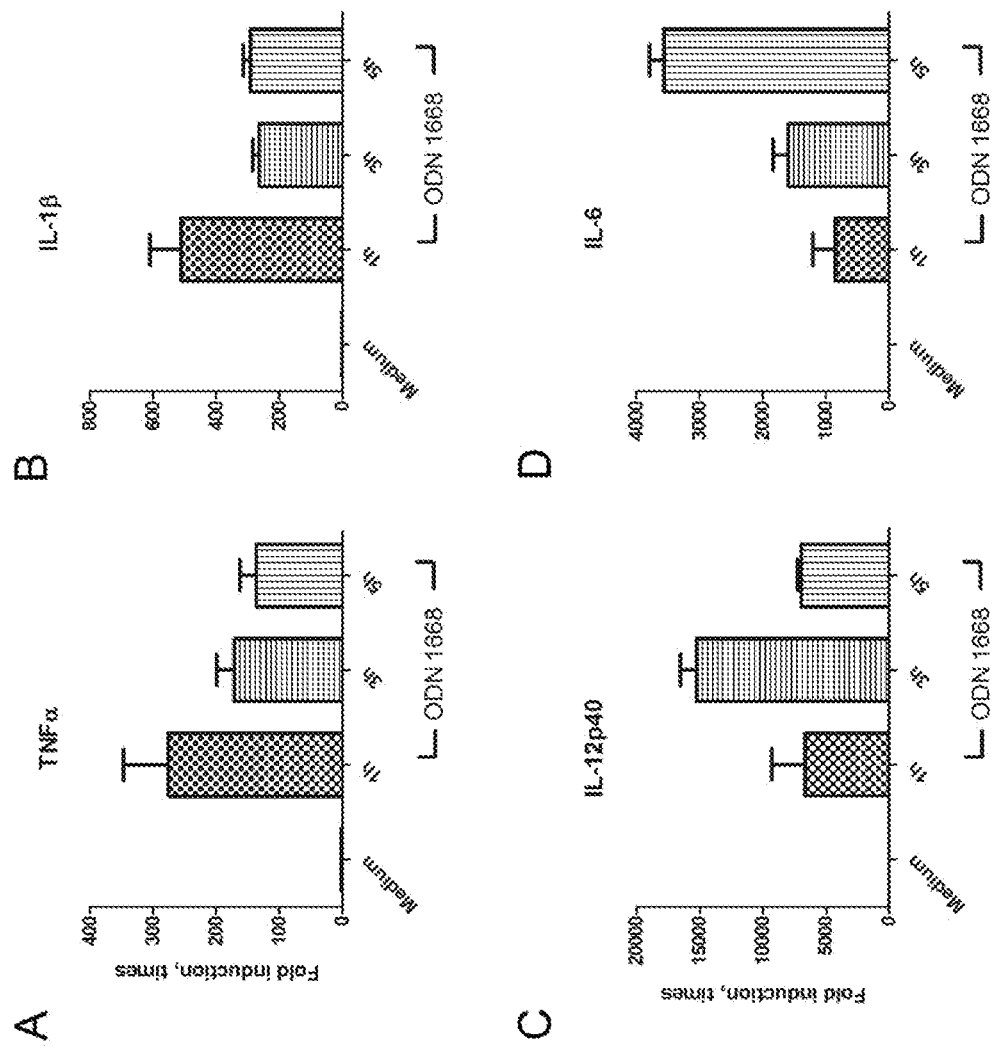
FIG. 5A, FIG. 5B, FIG. 5C, and FIG. 5D are bar graphs showing the kinetics of cytokine mRNA expression (FIG. 5A, TNFα.

Apparent discrepancy between effects of 9R9 on TNFα expression (FIG. 4) and secretion (FIG. 4) might be due to a weaker inhibitory potency of this peptide and the transitory nature of TNFαmRNA expression. Thus, the absence of 9R9 effects on TNFα contents in 5 hour supernatants indicates that the initial reduction of mRNA expression observed in 1 hour samples (FIG. 3) is compensated by elevated expression at the later time points (FIG. 5). Based on these results, CPDPs 9R34 and 9R11 were selected for further evaluation.

Figure 6:
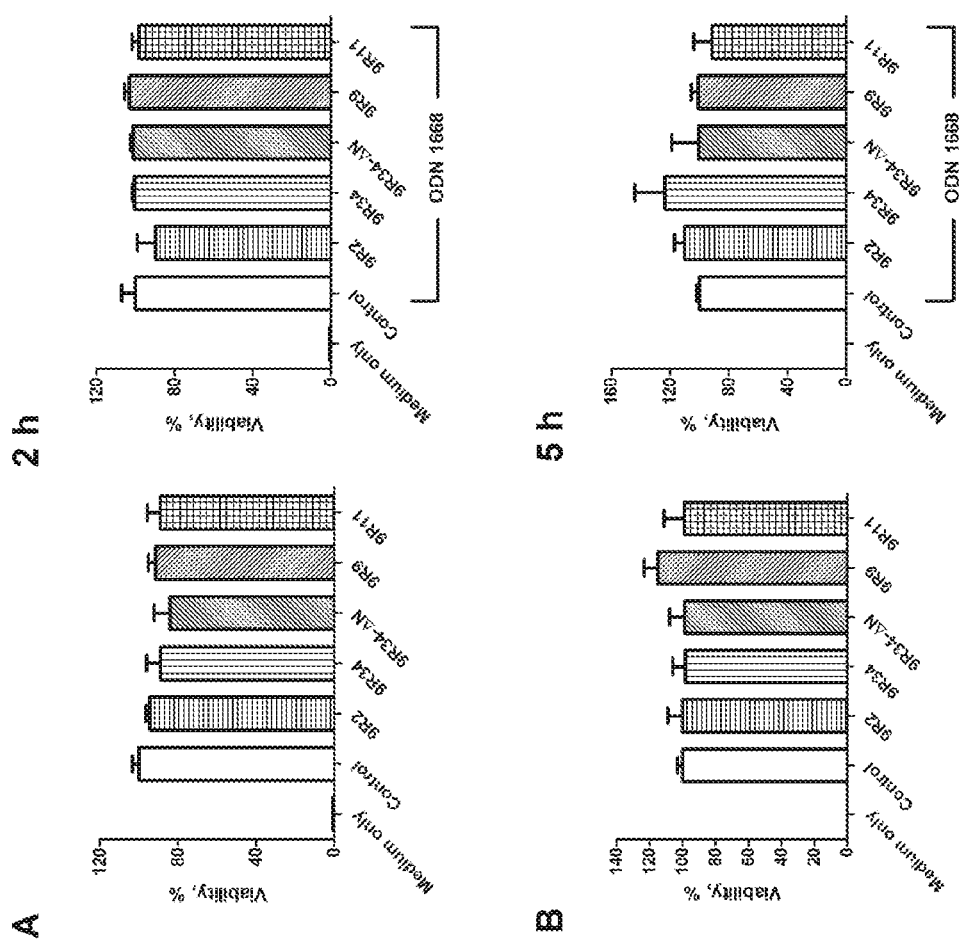
FIG. 6A and FIG. 6B are two sets of bar graphs showing the effects of decoy peptides on cell viability for the indicated time frames. The left panels show data without treatment with 2 μM ODN1668; the right panels show data with treatment with 2 μM ODN1668.

To exclude the possibility that the reduction in cytokine expression caused by peptides is due to general toxicity of inhibitory CPDPs we conducted the MTT cell viability assay. Inhibitory CPDP did not affect BMDM viability in a measurable way with or without concurrent TLR9 stimulation in all experimental conditions tested (FIG. 6). THP-1 macrophages were incubated with TLR9 inhibitory decoy peptides at 40 μM for 2 (FIG. 6A) or 5 hours (FIG. 6B) with (right panels) or without (left panels) treatment with ODN1668 at 2 μM. Cell viability was determined using 3-[4,5-dimethylthiazol-2-yl]-2,5 diphenyltetrazolium bromide (MTT) incorporation assay. Data were collected in 3 independent experiments.

Figure 7:
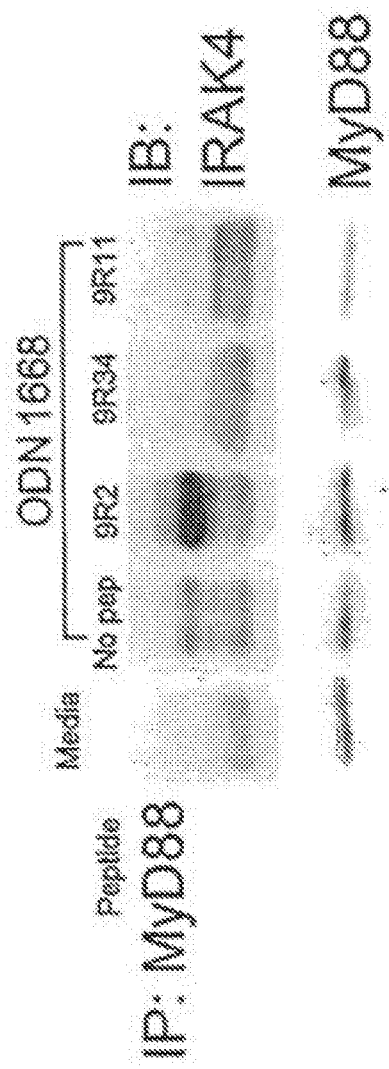
FIG. 7 is a western blot visualized with anti-IRAK4 antibody.

TLR stimulation causes formation of myDDosome, a signaling complex composed through interactions of IRAK and MyD88 death domains. To test if peptides inhibit myDDosome formation, MyD88 was immunoprecipitated from lysates of ODN-stimulated BMDM and the precipitates analyzed for IRAK4 presence. BMDM were lysed and immunoprecipitated with anti-MyD88 Ab and immune complexes assessed with anti-IRAK4 Ab 3 hours after cell treatment with ODN 1668. The data in FIG. 7 show a representative blot of two separate experiments. Pretreatment of BMDMs with CPDPs 9R34 or 9R11, but not with control peptide 9R2, prevented ODN 1668-induced myDDosome formation (see FIG. 7). FIG. 2 shows segments of TIR domains represented by CPDPs. FIG. 2B shows the positions of inhibitory peptides 9R34, 9R9, and 9R11.

Example 3. Specificity of TLR Inhibition by TLR9-Derived CPDP

Figure 8:
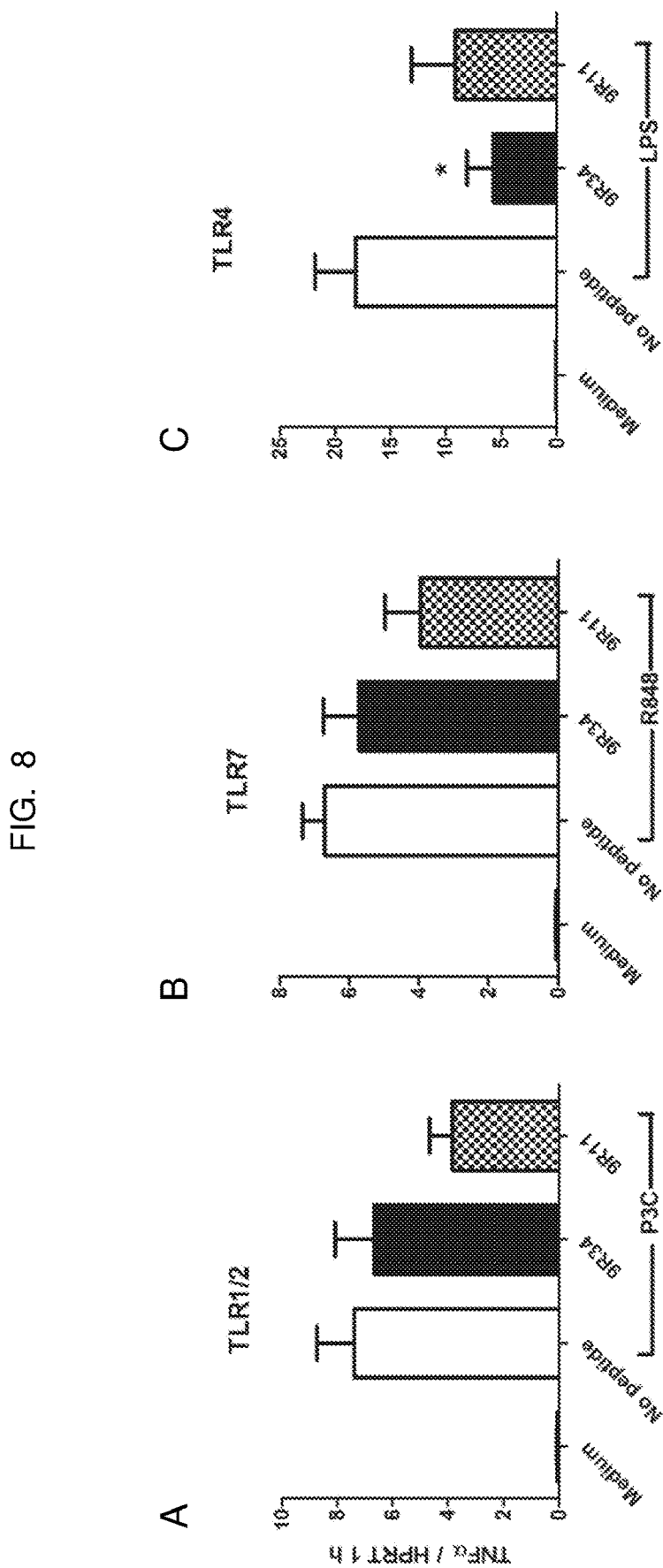
FIG. 8A, FIG. 8B, and FIG. 8C are bar graphs showing TNFαmRNA expression after cells, stimulated with agonists of different TLRs, were exposed to the indicated inhibitory peptides.

CPDPs 9R34 and 9R11 were examined for inhibition of TLR1/2, TLR4, and TLR7 signaling. BMDMs were stimulated with Pam3C, E. coli LPS, or R848 and TNFαmRNA was measured 1 hour after stimulation. Mouse BMDM were treated with 40 μM of the indicated peptides for 30 minutes prior to stimulation with ODN 1668 (1 μM), E. coli LPS (0.1 μg/mL), R848 (2.85 μM), or P3C (0.33 μM). R848 and P3C were used to specifically activate TLR7 and TLR2 signaling, respectively. TNFαmRNA expression was measured 1 h after ODN 1668 challenge and normalized to the expression of HPRT. See results in FIG. 8A, FIG. 8B, and FIG. 8C. TLR9 inhibitory peptides did not inhibit signaling induced by TLR1/2 or TLR7 agonist. Peptide treatment reduced the TNFαmRNA expression in LPS-stimulated cells by -50-70% (see FIG. 8). This level of inhibition of the LPS-stimulated expression was significantly less than that of the ODN-stimulated expression, in which case more than 99% of expression was inhibited (FIG. 3). Data show means±SEM of at least three independent experiments. The statistical significance of changes was determined by a one-way ANOVA test; *p<0.01.

Figure 9:
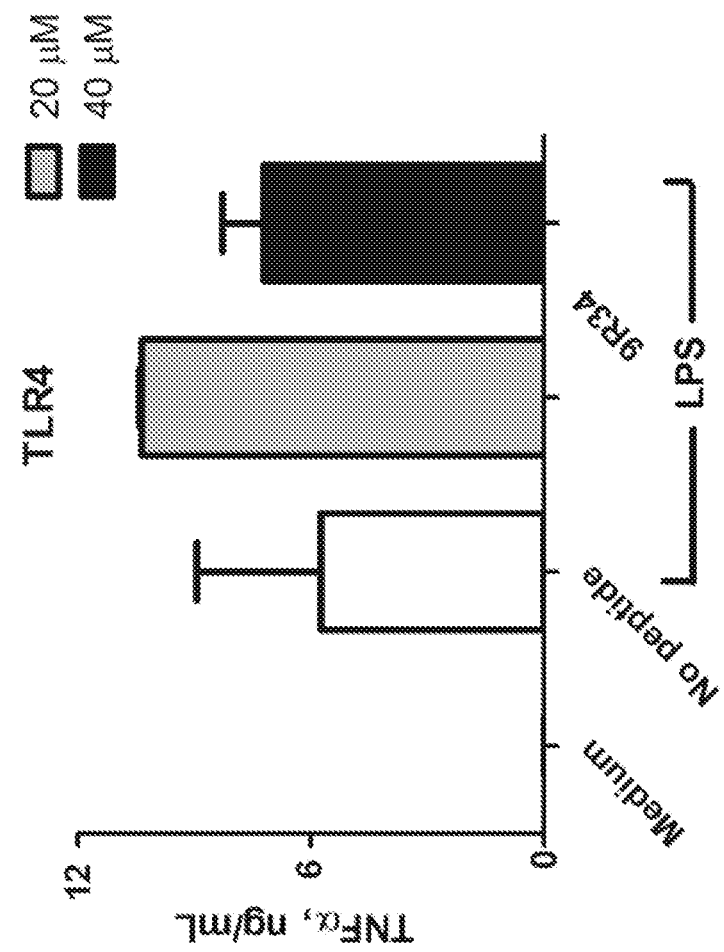
FIG. 9 is a bar graph showing TNFα concentration 5 hour after cell stimulation.

Additional verification of 9R34 effect by cytokine secretion did not show the inhibitory action on LPS-induced TNFαproduction in BMDM. BMDM were treated with 20 or 40 μM of 9R34 for 30 minutes prior to stimulation with E. coli LPS (0.1 μg/mL). TNFαconcentration in supernatants was evaluated by ELISA 5 hours after cell stimulation. See results in FIG. 9. Data represent means±SEM of three independent experiments. 9R34 did not reduce the LPS-induced TNFαsecretion measured in 5 hour BMDM supernatants, suggesting that the 9R34 effects on the LPS-induced TNFαmRNA is transient.

Example 4. Effects of Modified 9R34 Peptides on ODN 1668-Induced Cytokine Expression The experiments described herein suggest that 9R34 is the most potent inhibitor from the peptides screened. However, millimolar stock solutions of this peptide were unstable; the peptide solutions were also unstable in the presence of high protein concentrations. Therefore, several modifications of 9R34 were generated to determine more precisely the epitopes responsible for signaling inhibition and to improve peptide solubility. The inhibitory potency of modified peptides was compared with that of the parent peptide.

Five modifications of 9R34 were tested. Two modifications, 9R34-ΔN and 9R34-AC, are 9R34 deletion variants that were shortened by three amino acids at either N or C terminus. Three other modifications contained single amino acid replacements. 9R34-C/S had cysteine substituted for serine. 9R34-AL1 and 9R34-AL2 had one or two middle sequence leucines replaced by alanines (see Table 2, below).

TABLE 2

Peptide Sequences, Including 9R34 Variation Peptides.

| Peptide | Sequence | SEQ ID NOs |
|---|---|---|
| 9R2 | DKTQSAVADWVYNE | 3 |
| 9R34 | GRWALRLCLEERD | 6 |
| 9R34-ΔN | ALRLCLEERD | 8 |
| 9R34-ΔC | GRWALRLCLE | 10 |
| 9R34-C/S | GRWALRLSLEERD | 12 |
| 9R34-ΔL1 | GRWALRACLEERD | 14 |
| 9R34-ΔL2 | GRWALRACAEERD | 15 |

Figure 10:
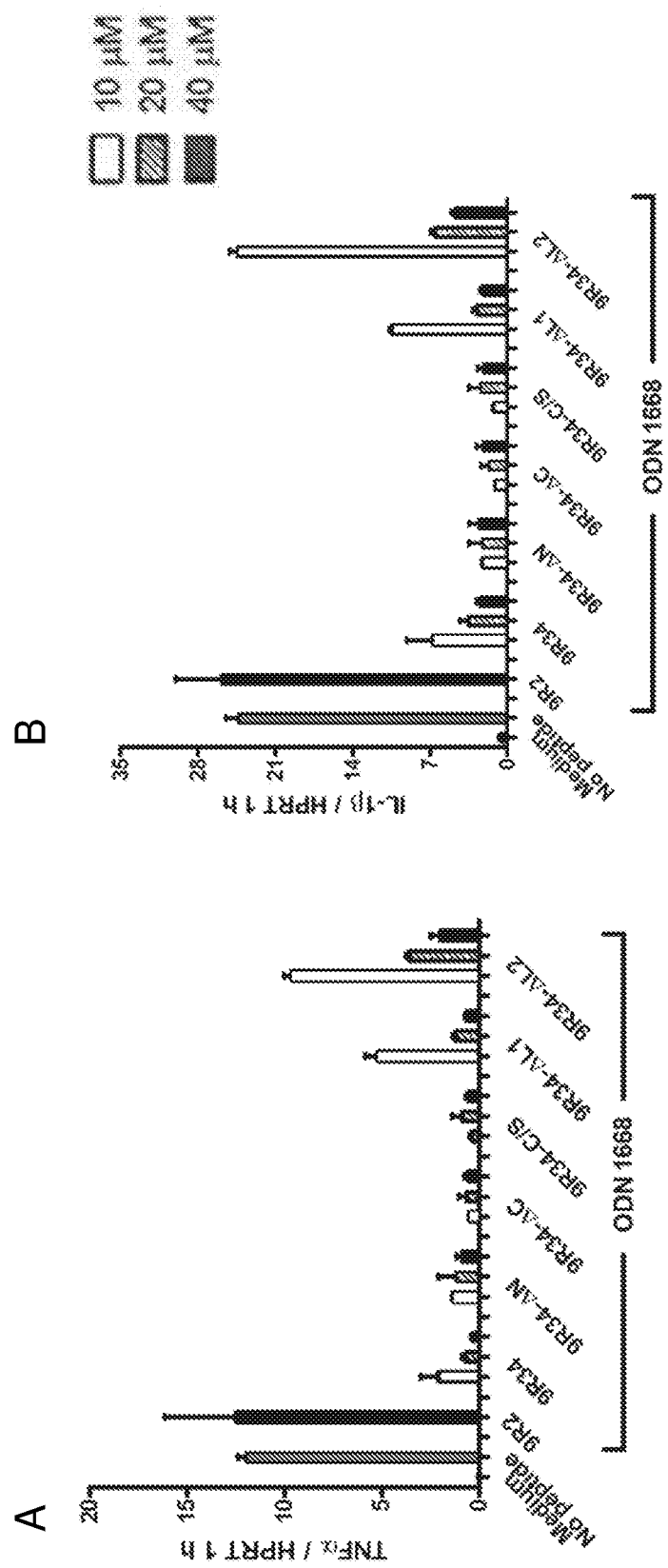
FIG. 10A, FIG. 10B, and FIG. 10C are bar graphs showing TNFα, IL-10, and IL-12-p40 mRNA expression, respectively, by ODN1668-stimulated macrophages treated with different modified peptides of 9R34.
Figure 10:
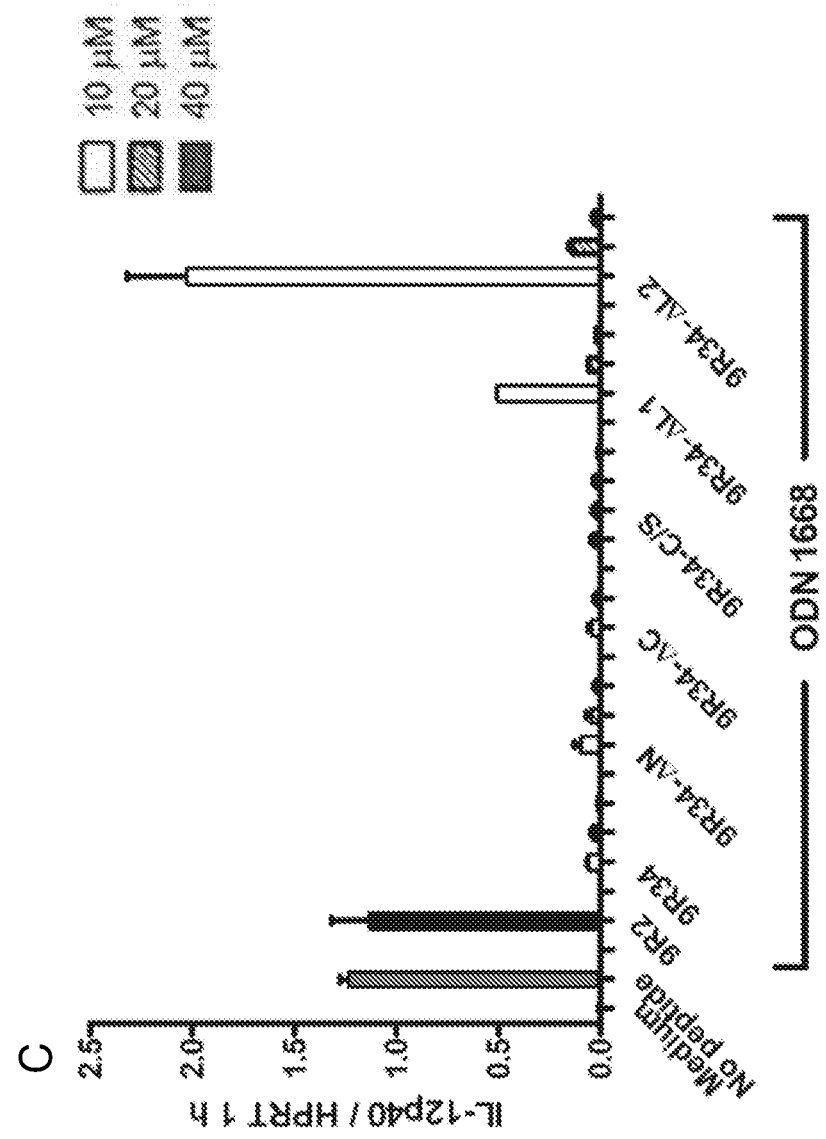

To investigate inhibition of TLR9 signaling by 9R34 analogues, the following work was performed. Mouse BMDMs were incubated in the presence of a 10, 20 or 40 µM decoy peptide for 30 minutes prior to stimulation with ODN 1668 (1 µM). Cytokine mRNA expression was measured 1 hour after ODN 1668 challenge and normalized to the expression of HPRT. CPDP sequences are shown in Table 2. See also Table 1. Results are presented in FIG. 10. Data represent means±SEM of at least three independent experiments.

The results suggested that 9R34-ΔN, 9R34-AC and 9R34C/S were as potent as the parent peptide, whereas 9R34-AL1 and 9R34-AL2 inhibited TLR9 signaling less potently. The 9R34-ΔN stock solutions were stable at concentrations up to 10 mM. This peptide remained soluble in bovine serum at high micromolar concentrations. These observations show that 9R34 inhibits TLR9 signaling sequence-specifically and suggest that 9R34-ΔN is better suited for in vivo applications.

Example 5. Effect of Cy3-Labeled CPDPs on Cer Fluorescence Lifetime

To identify potential binding partners of inhibitory peptides a FRET approach coupled with Fluorescence Lifetime Imaging Microscopy (FLIM) was used. HeLa cells were transiently transfected with an expression vector that encodes a TIR domain fused with Cerulean fluorescent protein (Cer). Cells were treated with various concentrations of a Cy3-labeled inhibitory peptide 48 hours after transfection. Cy3 is a suitable FRET acceptor for Cer fluorescence. A direct molecular interaction of a Cy3-labeled peptide with Cer-fused TIR domain should quench Cer fluorescence, leading to a decreased fluorescence lifetime.

TLR9, MyD88, and TIRAP were selected as potential primary binding partners for Cy3-9R34-ΔN and Cy3-9R11. Cer-fused TLR2 and TLR4 TIR domains, and Cer not fused to a TIR, were used as controls. It was previously demonstrated that the TLR2-derived peptide 2R9 binds TIRAP TIR. Therefore, the TIRAP-Cer with Cy3-2R9 was used as a positive binding control. Binding of Cy3-labeled CPDPs to Cerulean- (Cer-) labeled TIR domains was tested as follows. Fluorescence Lifetime IMages (FLIM) were made of HeLa cells expressing Cer not fused with a TIR domain (upper row) or fused with TLR9 TIR or TIRAP TIR (middle and bottom rows) and treated with a Cy3-labeled decoy peptide for 1 hour. Results are shown in FIG. 11.

FIG. 11 shows FLIM images of HeLa cells transfected with different Cer-TIR constructs as indicated and treated with inhibitory peptides at various concentrations. The images show the average fluorescence lifetime of Cer component calculated on the pixel-by-pixel basis using the bi-exponential model with one component having a fixed lifetime. Shorter fluorescence lifetimes indicate quenching of Cer fluorescence caused by direct TIR-peptide binding.

The histograms in FIG. 12 show the frequencies of occurrence of particular average lifetimes in the images shown in FIG. 11. A progressive shift of average fluorescence lifetime towards lower values observed with increasing peptide concentrations indicates the binding between donor and acceptor moieties. A larger decrease in average lifetime corresponds to a larger number of donor-acceptor pairs present within the sample, indicating an effective FRET (see FIG. 13). FIG. 13 shows results for FRET efficiency for different TIR-peptide pairs. FRET efficiencies presented in FIG. 13 were calculated from the average lifetimes corresponding to entire images that contained multiple cells as in images shown in FIG. 11, using data obtained in three independent experiments. Data represent means±SEM of two independent experiments.

The strongest peptide-induced quenching was detected for the TLR9 TIR-Cer-expressing cells treated with Cy3-9R34-ΔN. This peptide quenched the TLR9 TIR-Cer fluorescence dose-dependently with FRET efficiency varying in the range of 9-23% (FIG. 13). Fluorescence lifetime of TLR9 TIR-Cer construct was decreased even in cells treated with the minimal peptide concentration used (2.5 µM) (FIG. 11, FIG. 12, and FIG. 13). Cy3-9R34-ΔN also notably quenched the fluorescence of cells that expressed the TIRAP-Cer (FIG. 13). The Cy3-9R34-ΔN effect on TIRAP-Cer fluorescence was weaker than on that of the TLR9 TIR-Cer, as suggested by the absence of the effect of the lowest peptide concentration (FIG. 13). The quenching observed for the control TIR-peptide pair, TIRAP-2R9, was slightly higher than for the TLR9-9R34-ΔN pair (FIG. 11, FIG. 12, and FIG. 13). The average fluorescence lifetime of Cer-labeled MyD88 TIR was not affected by Cy3-9R34-ΔN at lower peptide concentrations (2.5 and 10 µM) (FIG. 13). The quenching of MyD88 TIR-Cer was notable at 40 µM peptide concentration, but considerably less in comparison with the effect on TLR9 and TIRAP TIR-Cer (FIG. 13). Cy3-9R34-ΔN at 40 µM also slightly affected the fluorescence lifetime of control TLR2 TIR-Cer, TLR4 TIR-Cer, TRAM-Cer, and Cer not fused to a TIR domain (see FIG. 11, FIG. 12, and FIG. 13). The effects on these constructs show the level of unspecific quenching of Cer by Cy3-labeled peptides at high peptide concentrations.

Cy3-9R11 dose-dependently quenched the fluorescence of TLR9 TIR-Cer with FRET efficiency varying in the range of 3-27%; in addition, Cy3-9R11 induced FRET from TIRAP-Cer, but only when used at higher concentrations of 10 or 40 µM (FIG. 13). The quenching of MyD88-Cer fluorescence lifetime by Cy3-9R11 was also detectable, but less effective. Unspecific Cer quenching by Cy3-9R11 was observed at a peptide concentration of 40 µM, similarly to the effects of Cy3-9R34-ΔN.

In summary, the FLIM experiments suggest that both 9R34-ΔN and 9R11 bind TLR9 and TIRAP TIR. 9R11 also interacted with the MyD88 TIR, but with a lower affinity, whereas 9R34-ΔN did not interact with MyD88.

Example 6. 9R34-ΔN Inhibits ODN 1668-Induced Systemic Cytokines In Vivo and Protects Against TLR9-Induced Lethality To test the in vivo efficacy and specificity of 9R34-ΔN, C57BL/6J mice were mock-treated or treated i.p. with a single dose of inhibitory or control peptide (200 nmol/mouse) and challenged with TLR9 agonist ODN 1668 (7.86 nmol/mouse) or TLR2/1 agonist Pam3C (67 nmol/mouse) 1 hour later. Plasma concentrations of TNFα and IL-12-p40 were measured 1, 3, and 5 hours after the challenge. Both TLR agonists increased concentrations of TNFα and IL-12-p40 in 1 hour samples from below the limit of detection to about 1.2 and about 6 ng/mL in the case of ODN 1668, and to 0.12 ng/mL and 1 ng/mL after treatment with Pam3C. See FIG. 14.

Plasma TNFα and IL-12-p40 levels following intraperitioneal administration of ODN 1668 to C57Bl/6J mice in peptide-pretreated and control mice are shown in FIG. 14A and FIG. 14B. The same data is presented following intraperitoneal administration of Pam3C is shown in FIG. 14C and FIG. 14D. Data shown in these figures represent the means±SEM obtained in at least three independent experiments. The statistical significance of changes in cytokine concentrations was determined by a two-way ANOVA test; *p<0.001.

Figure 14:
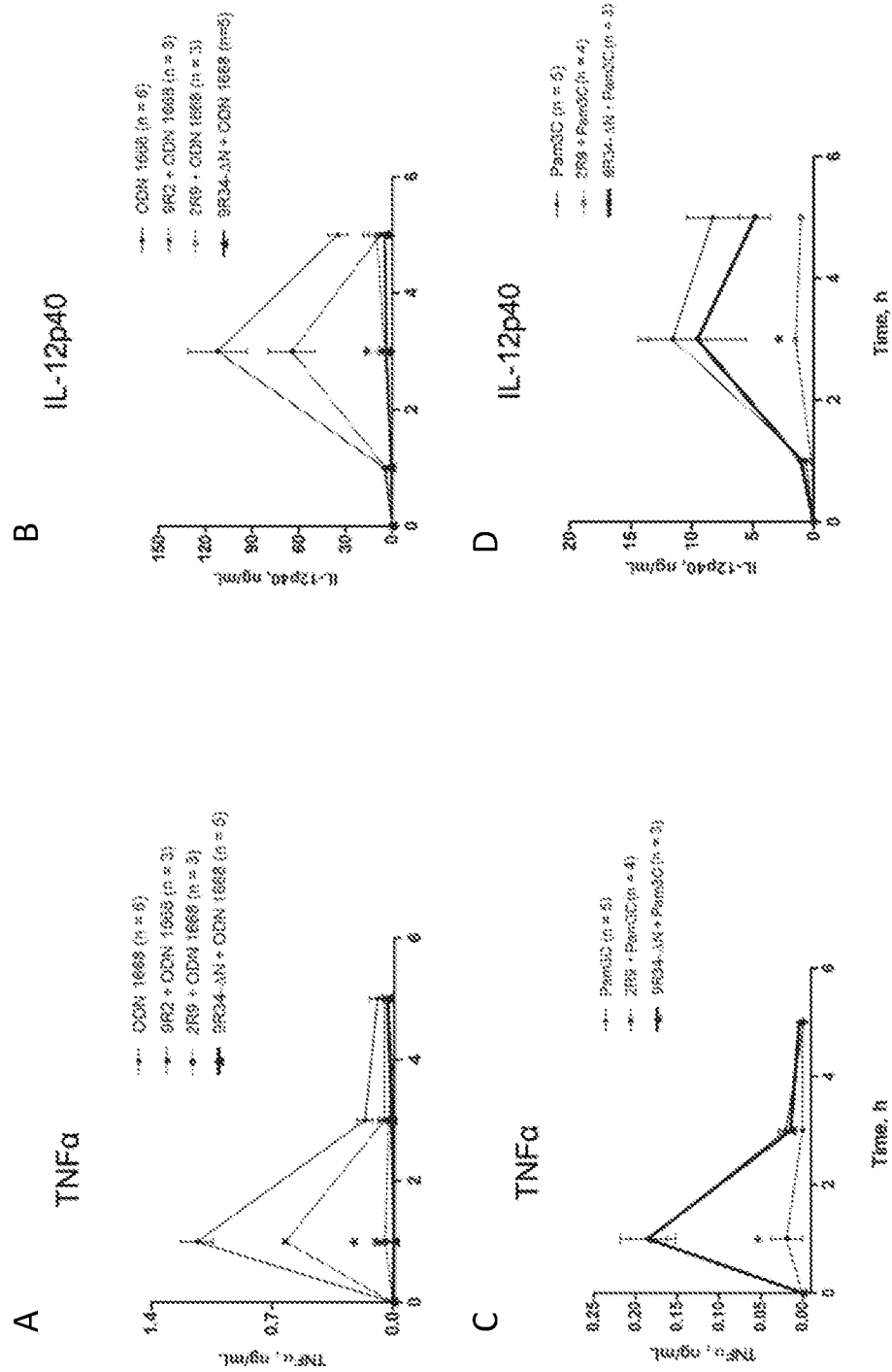
FIG. 14A and FIG. 14B are graphs showing plasma TNFα and IL-12-p40 levels, respectively, following administration of ODN1668 to C57BL/6J mice mock-treated with PBS or treated with inhibitory peptides.
FIG. 14C and FIG. 14D are graphs showing plasma TNFα and IL-12-p40 levels, respectively, following administration of Pam3C to the C57BL/6J mice mock-treated with PBS or treated with inhibitory peptides.
FIG. 14E and FIG. 14F are graphs showing the survival of D-Gal pretreated mice after treatment with ODN1668 and peptides.
Figure 14:
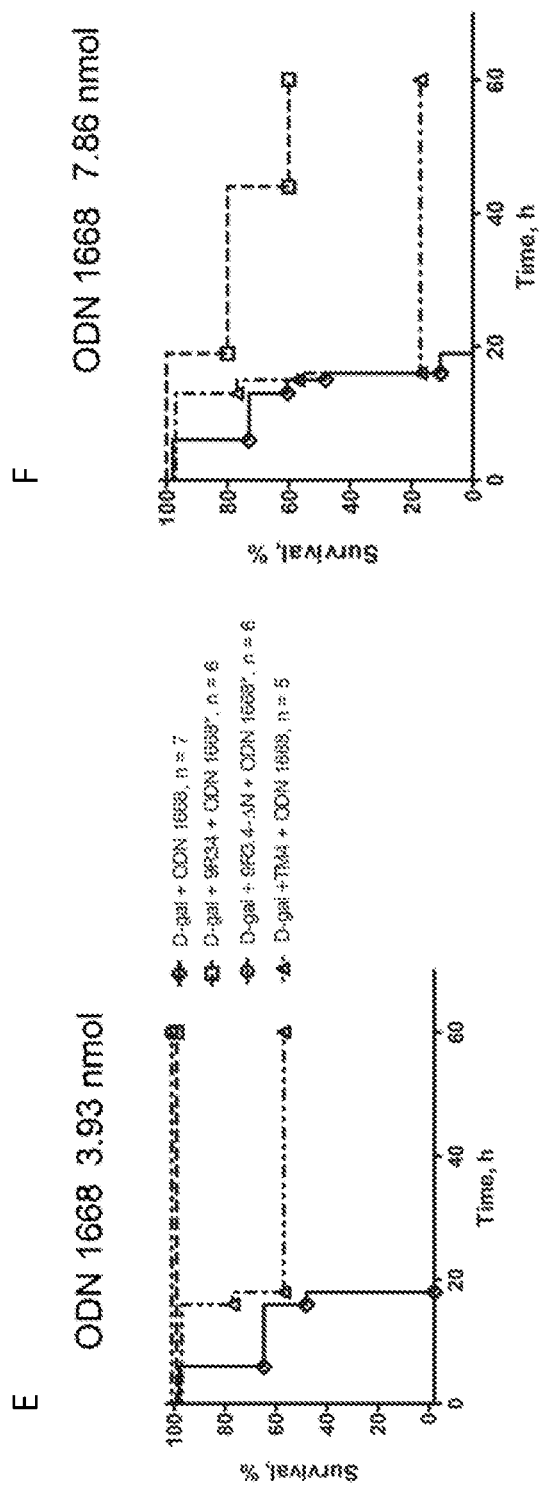

The concentration of TNFα dropped rapidly to near basal levels in 3-hour samples, whereas circulating IL-12-p40 continued to grow and increased more than ten-fold in next two hours, peaking at about 110 ng/mL in the ODN 1668-treated mice and at about 11 ng/mL in mice challenged with Pam3C (see FIG. 14). ODN 1668-treated mice pretreated with 9R34-ΔN eliminated the 1-hour TNFα peak and decreased the IL-12-p40 peak by approximately 25-fold in the 3-hour samples (FIG. 14A and FIG. 14B). In a sharp contrast to the effect on the ODN-induced cytokines, 9R34-ΔN did not affect cytokine levels induced by TLR2 agonist Pam3C (FIG. 14C and FIG. 14D), thereby confirming the cell culture data presented above. Previous studies have identified 2R9, a TLR2-derived peptide that inhibits TLR2, TLR4, TLR7, and TLR9, primarily because it targets an adapter shared by these TLRs. As expected, 2R9 suppressed cytokine induction elicited by either ODN 1668 or Pam3C; whereas 9R34-ΔN selectively inhibited only the ODN 1668-induced cytokines (see FIG. 14A, FIG. 14B, FIG. 14C and FIG. 14D). Negative control peptide 9R2 (which did not inhibit TLR9 in cell culture experiments) was tested in vivo only with respect to ODN-induced cytokines; as expected, 9R2 did not significantly reduce the ODN-induced cytokine levels in mice (see FIG. 14). These data clearly demonstrate that TLR9 inhibition by 9R34-ΔN is selective.

Example 7. Survival of D-Gal Pretreated Mice after Treatment with ODN 1668

With the exception for LPS, administration of a purified TLR agonist is not lethal to mice. Mice, however, can be sensitized to TLR agonists by pretreatment with D-galactosamine (D-Gal). Survival of C57Bl/6J mice pretreated with D-galactosamine and challenged with different doses of ODN 1668 was tested. Mice were first administered with D-Gal intraperitoneally at the dose of 20 mg/mouse. Thirty minutes later mice were mock-treated with PBS or treated with a CPDP at the dose 200 nmol/mouse. ODN 1668 was administered 1 hour after peptide treatment at the dose of 3.93 or 7.86 nmol/mouse.

Results are shown in FIG. 14E and FIG. 14F. The statistical significance of changes in mortality and survival time was determined by the Gehan-Breslow-Wilcoxon test; *p<0.01. Peptides 9R2 (FIG. 14A, FIG. 14B) and TM4 (FIG. 14C, FIG. 14D) were used as the control peptides. Either ODN 1668 dose used induced 100% lethality in the D-Gal-pretreated mice. 9R34 or 9R34-ΔN administered intraperitoneally provided full protection to mice that received ODN 1668 at the lower dose of 3.93 nmol/mouse (FIG. 14E and FIG. 14F). TM4, a potent inhibitor of TLR4 derived from TRAM, fully protected mice against mortality caused by LPS. TM4 was less effective than 9R34-ΔN in protection against ODN-induced lethality. Both 9R34-ΔN and TM4 were less protective, when tested in mice treated with a higher ODN1668 dose (50 µg/mouse) (see FIG. 14E and FIG. 14F). Nevertheless, 9R34-ΔN rescued more than 50% of mice (see FIG. 14E and FIG. 14F). These data indicate that 9R34-ΔN protects mice from TLR9-induced lethality. Partial protection observed after TM4 treatment apparently is due to suppression of TLR4-mediated inflammatory response and consequent injury caused by endogenous danger-associated molecules that may be produced in the body in response to mechanical, chemical, or biological injury.

Example 8. Comparison of Commercially Available TLR9 Inhibitor ODN INH-18 with 9R34

To investigate inhibition of TLR9 signaling by 9R34 further, the following work was conducted. Mouse BMDMs were treated with the effective dose of either INH-18 (an ODN-based, competitive inhibitor of TLR9, commercially available through Invivogen™) or 9R34, 30 minutes prior to stimulation with varying concentration of ODN 1668. TNFα mRNA expression was measured 1 hour after ODN 1668 challenge and normalized to the expression of HPRT.

Figure 15:
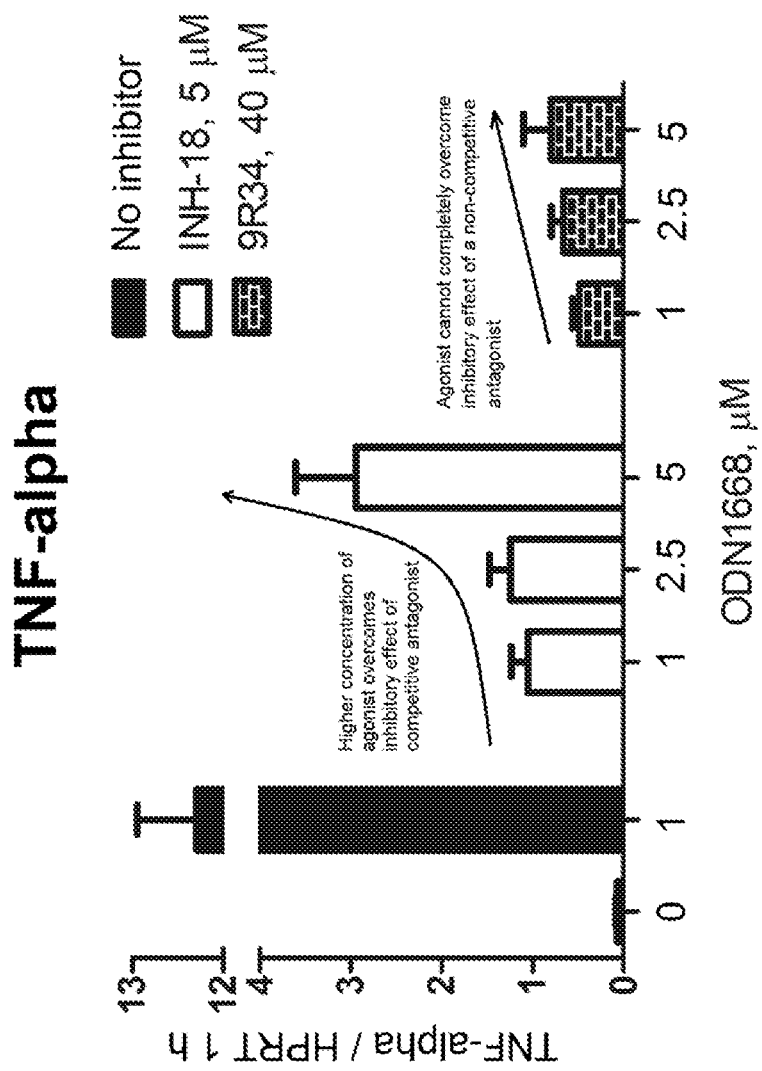
FIG. 15 is a bar graph showing TNFα/HPRT mRNA expression ration versus ODN1688 concentration in cells treated with competitive and non-competitive TLR9 inhibitor.

Results are presented in FIG. 15. The increased concentrations of agonistic ODN led to a significantly steeper increase in the TNFα/HPRT mRNA expression ratio in cells treated with INH 18 than in the 9R34-treated cells. These data show that an increase of agonist concentration overcomes TLR9 inhibition by ODN INH-18, a competitive inhibitor of TLR9, but much less so the inhibition by 9R34, thereby indicating that 9R34 has an advantage of providing the efficient inhibition in a wider range of agonist concentrations, compared to INH 18.

REFERENCES

All references listed below and throughout the specification are hereby incorporated by reference in their entirety.
1. Allette, Y. M., Y. Kim, A. L. Randolph, J. A. Smith, M. S. Ripsch, and F. A. White. 2017. Decoy peptide targeted to Toll-IL-1R domain inhibits LPS and TLR4-active metabolite morphine-3 glucuronide sensitization of sensory neurons. *Sci Rep* 7:3741.
2. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. *Nucleic Acids Res* 25:3389-3402.
3. Ashkar, A. A., and K. L. Rosenthal. 2002. Toll-like receptor 9, CpG DNA and innate immunity. *Curr Mol Med* 2:545-556.
4. Barrat, F. J., T. Meeker, J. Gregorio, J. H. Chan, S. Uematsu, S. Akira, B. Chang, O. Duramad, and R. L. Coffman. 2005. Nucleic acids of mammalian origin can act as endogenous ligands for Toll-like receptors and may promote systemic lupus erythematosus. *J Exp Med* 202: 1131-1139.
5. Bhattacharyya, S., and J. Varga. 2015. Emerging roles of innate immune signaling and toll-like receptors in fibrosis and systemic sclerosis. *Curr Rheumatol Rep* 17:474.

6. Bonham, K. S., M. H. Orzalli, K. Hayashi, A. I. Wolf, C. Glanemann, W. Weninger, A. Iwasaki, D. M. Knipe, and J. C. Kagan. 2014. A promiscuous lipid-binding protein diversifies the subcellular sites of toll-like receptor signal transduction. *Cell* 156:705-716.
7. Botos, I., D. M. Segal, and D. R. Davies. 2011. The structural biology of Toll-like receptors. *Structure* 19:447-459.
8. Celhar, T., and A. M. Fairhurst. 2014. Toll-like receptors in systemic lupus erythematosus: potential for personalized treatment. *Front Pharmacol* 5:265.
9. Ciechomska, M., R. Cant, J. Finnigan, J. M. van Laar, and S. O'Reilly. 2013. Role of toll-like receptors in systemic sclerosis. *Expert Rev Mol Med* 15:e9.
10. Connolly, D. J., and L. A. O'Neill. 2012. New developments in Toll-like receptor targeted therapeutics. *Current opinion in pharmacology* 12:510-518.
11. Cook, D. N., D. S. Pisetsky, and D. A. Schwartz. 2004. Toll-like receptors in the pathogenesis of human disease. *Nat Immunol* 5:975-979.
12. Couture, L. A., W. Piao, L. W. Ru, S. N. Vogel, and V. Y. Toshchakov. 2012. Targeting Toll-like receptor (TLR) signaling by Toll/interleukin-1 receptor (TIR) domain-containing adapter protein/MyD88 adapter-like (TIRAP/Mal)-derived decoy peptides. *J Biol Chem* 287:24641-24648.
13. Curtiss, L. K., and P. S. Tobias. 2009. Emerging role of Toll-like receptors in atherosclerosis. *J Lipid Res* 50 Suppl:S340-345.
14. Derossi, D., A. H. Joliot, G. Chassaing, and A. Prochiantz. 1994. The third helix of the Antennapedia homeodomain translocates through biological membranes. *J Biol Chem* 269:10444-10450.
15. Duffy, L., and S. C. O'Reilly. 2016. Toll-like receptors in the pathogenesis of autoimmune diseases: recent and emerging translational developments. *Immunotargets Ther* 5:69-80.
16. Dunne, A., M. Ejdeback, P. L. Ludidi, L. A. O'Neill, and N. J. Gay. 2003. Structural complementarity of Toll/interleukin-1 receptor domains in Toll-like receptors and the adaptors Mal and MyD88. *J Biol Chem* 278:41443-41451.
17. Falck-Hansen, M., C. Kassiteridi, and C. Monaco. 2013. Toll-like receptors in atherosclerosis. *Int J Mol Sci* 14:14008-14023.
18. Ferrao, R., J. Li, E. Bergamin, and H. Wu. 2012. Structural insights into the assembly of large oligomeric signalosomes in the Toll-like receptor-interleukin-1 receptor superfamily.
Science signaling 5:re3.
19. Gay, N. J., M. F. Symmons, M. Gangloff, and C. E. Bryant. 2014. Assembly and localization of Toll-like receptor signalling complexes. *Nat Rev Immunol* 14:546-558.
20. Guex, N., and M. C. Peitsch. 1997. SWISS-MODEL and the Swiss-PdbViewer: an environment for comparative protein modeling. *Electrophoresis* 18:2714-2723.
21. Han, K. J., X. Su, L. G. Xu, L. H. Bin, J. Zhang, and H. B. Shu. 2004. Mechanisms of the TRIF-induced interferon-stimulated response element and NF-kappaB activation and apoptosis pathways. *J Biol Chem* 279:15652-15661.
22. Hatai, H., A. Lepelley, W. Zeng, M. S. Hayden, and S. Ghosh. 2016. Toll-Like Receptor 11 (TLR11) Interacts with Flagellin and Profilin through Disparate Mechanisms. *PLoS One* 11:e0148987.
23. Hedhli, D., N. Moire, H. Akbar, F. Laurent, B. Heraut, I. Dimier-Poisson, and M. N. Mevelec. 2016. The antigen-specific response to *Toxoplasma gondii* profilin, a TLR11/12 ligand, depends on its intrinsic adjuvant properties. *Med Microbiol Immunol* 205:345-352.
24. Hirschfeld, M., Y. Ma, J. H. Weis, S. N. Vogel, and J. J. Weis. 2000. Cutting edge: repurification of lipopolysaccharide eliminates signaling through both human and murine toll-like receptor 2. *J Immunol* 165:618-622.
25. Horng, T., G. M. Barton, and R. Medzhitov. 2001. TIRAP: an adapter molecule in the Toll signaling pathway. *NatImmunol* 2:835-841.
26. Horng, T., G. M. Barton, R. A. Flavell, and R. Medzhitov. 2002. The adaptor molecule TIRAP provides signalling specificity for Toll-like receptors. *Nature* 420:329-333.
27. Hu, X., Y. Fu, Y. Tian, Z. Zhang, W. Zhang, X. Gao, X. Lu, Y. Cao, and N. Zhang. 2016. The anti-inflammatory effect of TR6 on LPS-induced mastitis in mice. *Int Immunopharmacol* 30:150-156.
28. Hu, X., Y. Tian, S. Qu, Y. Cao, S. Li, W. Zhang, Z. Zhang, N. Zhang, and Y. Fu. 2017. Protective effect of TM6 on LPS-induced acute lung injury in mice. *Sci Rep* 7:572.
29. Huyton, T., J. Rossjohn, and M. Wilce. 2007. Toll-like receptors: structural pieces of a curve-shaped puzzle. *Immunol Cell Biol* 85:406-410.
30. Jiang, Z., P. Georgel, C. Li, J. Choe, K. Crozat, S. Rutschmann, X. Du, T. Bigby, S. Mudd, S. Sovath, I. A. Wilson, A. Olson, and B. Beutler. 2006. Details of Toll-like receptor:adapter interaction revealed by germ-line mutagenesis. *Proc Natl Acad Sci USA* 103:10961-10966.
31. Kagan, J. C., and R. Medzhitov. 2006. Phosphoinositide-mediated adaptor recruitment controls Toll-like receptor signaling. *Cell* 125:943-955.
32. Kawai, T., and S. Akira. 2011. Toll-like receptors and their crosstalk with other innate receptors in infection and immunity. *Immunity* 34:637-650.
33. Ke, Y., W. Li, Y. Wang, M. Yang, J. Guo, S. Zhan, X. Du, Z. Wang, M. Yang, J. Li, W. Li, and Z. Chen. 2016. Inhibition of TLR4 signaling by *Brucella* TIR-containing protein TcpB-derived decoy peptides. *Int J Med Microbiol* 306:391-400.
34. Kim, M. H., D. S. Yoo, S. Y. Lee, S. E. Byeon, Y. G. Lee, T. Min, H. S. Rho, M. H. Rhee, J. Lee, and J. Y. Cho. 2011. The TRIF/TBK1/IRF-3 activation pathway is the primary inhibitory target of resveratrol, contributing to its broad-spectrum anti-inflammatory effects. *Pharmazie* 66:293-300.
35. Kirk, P., and J. F. Bazan. 2005. Pathogen recognition: TLRs throw us a curve. *Immunity* 23:347-350.
36. Koblansky, A. A., D. Jankovic, H. Oh, S. Hieny, W. Sungnak, R. Mathur, M. S. Hayden, S. Akira, A. Sher, and S. Ghosh. 2013. Recognition of profilin by Toll-like receptor 12 is critical for host resistance to *Toxoplasma gondii*. Immunity 38:119-130.
37. Kornblit, B., and K. Muller. 2017. Sensing danger: toll-like receptors and outcome in allogeneic hematopoietic stem cell transplantation. *Bone Marrow Transplant* 52:499-505.
38. Lai, Y., and R. L. Gallo. 2008. Toll-like receptors in skin infections and inflammatory diseases. *Infect Disord Drug Targets* 8:144-155.
39. Latty, S., J. Sakai, L. Hopkins, B. Verstak, T. Paramo, N. A. Berglund, N. J. Gay, P. J. Bond, D. Klenerman, and C. E. Bryant. 2018. Activation of Toll-like receptors nucleates assembly of the MyDDosome signaling hub. eLife 7.

40. Lin, S. C., Y. C. Lo, and H. Wu. 2010. Helical assembly in the MyD88-IRAK4-IRAK2 complex in TLR/IL-1R signalling. *Nature* 465:885-890.
41. Lysakova-Devine, T., B. Keogh, B. Harrington, K. Nagpal, A. Halle, D. T. Golenbock, T. Monie, and A. G. Bowie. 2010. Viral inhibitory peptide of TLR4, a peptide derived from vaccinia protein A46, specifically inhibits TLR4 by directly targeting MyD88 adaptor-like and TRIF-related adaptor molecule. *JImmunol* 185:4261-4271.
42. Medzhitov, R., and T. Horng. 2009. Transcriptional control of the inflammatory response. *Nat Rev Immunol* 9:692-703.
43. Monie, T. P., M. C. Moncrieffe, and N. J. Gay. 2009. Structure and regulation of cytoplasmic adapter proteins involved in innate immune signaling. *Immunol Rev* 227:161-175.
44. Motshwene, P. G., M. C. Moncrieffe, J. G. Grossmann, C. Kao, M. Ayaluru, A. M. Sandercock, C. V. Robinson, E. Latz, and N. J. Gay. 2009. An oligomeric signaling platform formed by the Toll-like receptor signal transducers MyD88 and IRAK-4. *J Biol Chem* 284:25404-25411.
45. Nakase, I., Y. Konishi, M. Ueda, H. Saji, and S. Futaki. 2012. Accumulation of arginine-rich cell-penetrating peptides in tumors and the potential for anticancer drug delivery in vivo. Journal of controlled release: official journal of the Controlled Release Society 159:181-188.
46. Narayanan, K. B., and H. H. Park. 2015. Toll/interleukin-1 receptor (TIR) domain-mediated cellular signaling pathways. *Apoptosis* 20:196-209.
47. Nunez Miguel, R., J. Wong, J. F. Westoll, H. J. Brooks, L. A. O'Neill, N. J. Gay, C. E. Bryant, and T. P. Monie. 2007. A dimer of the Toll-like receptor 4 cytoplasmic domain provides a specific scaffold for the recruitment of signalling adaptor proteins. *PloS one* 2:e788.
48. Ohto, U., T. Shibata, H. Tanji, H. Ishida, E. Krayukhina, S. Uchiyama, K. Miyake, and T. Shimizu. 2015. Structural basis of CpG and inhibitory DNA recognition by Toll-like receptor 9. *Nature* 520:702-705.
49. O'Neill, L. A., and A. G. Bowie. 2007. The family of five: TIR-domain-containing adaptors in Toll-like receptor signalling. *Nature reviews. Immunology* 7:353-364.
50. O'Neill, L. A., C. E. Bryant, and S. L. Doyle. 2009. Therapeutic targeting of Toll-like receptors for infectious and inflammatory diseases and cancer. *Pharmacological reviews* 61:177-197.
51. Oosting, M., S. C. Cheng, J. M. Bolscher, R. Vestering-Stenger, T. S. Plantinga, I. C. Verschueren, P. Arts, A. Garritsen, H. van Eenennaam, P. Sturm, B. J. Kullberg, A. Hoischen, G. J. Adema, J. W. van der Meer, M. G. Netea, and L. A. Joosten. 2014. Human TLR10 is an anti-inflammatory pattern-recognition receptor. *Proc Natl Acad Sci USA* 111:E4478-4484.
52. Pace, C. N., F. Vajdos, L. Fee, G. Grimsley, and T. Gray. 1995. How to measure and predict the molar absorption coefficient of a protein. *Protein Sci* 4:2411-2423.
53. Patterson, N. J., and D. Werling. 2013. To con protection: TIR-domain containing proteins (Tcp) and innate immune evasion. *Vet Immunol Immunopathol* 155:147-154.
54. Pettersen, E. F., T. D. Goddard, C. C. Huang, G. S. Couch, D. M. Greenblatt, E. C. Meng, and T. E. Ferrin. 2004. UCSF Chimera—a visualization system for exploratory research and analysis. *Journal of computational chemistry* 25:1605-1612.
55. Piao, W., L. W. Ru, K. H. Piepenbrink, E. J. Sundberg, S. N. Vogel, and V. Y. Toshchakov. 2013. Recruitment of TLR adapter TRIF to TLR4 signaling complex is mediated by the second helical region of TRIF TIR domain. *Proc Natl Acad Sci USA* 110:19036-19041.
56. Piao, W., S. N. Vogel, and V. Y. Toshchakov. 2013. Inhibition of TLR4 signaling by TRAM-derived decoy peptides in vitro and in vivo. *JImmunol* 190:2263-2272.
57. Piao, W. J., L. W. Ru, K. H. Piepenbrink, E. J. Sundberg, S. N. Vogel, and V. Y. Toshchakov. 2013. Recruitment of TLR adapter TRIF to TLR4 signaling complex is mediated by the second helical region of TRIF TIR domain. *P Natl Acad Sci USA* 110:19036-19041.
58. Piao, W., K. A. Shirey, L. W. Ru, W. Lai, H. Szmacinski, G. A. Snyder, E. J. Sundberg, J. R. Lakowicz, S. N. Vogel, and V. Y. Toshchakov. 2015. A Decoy Peptide that Disrupts TIRAP Recruitment to TLRs Is Protective in a Murine Model of Influenza. *Cell reports* 11:1941-1952.
59. Piao, W., L. W. Ru, and V. Y. Toshchakov. 2016. Differential adapter recruitment by TLR2 co-receptors. Pathogens and disease 74.
60. Remmert, M., A. Biegert, A. Hauser, and J. Soding. 2011. HHblits: lightning-fast iterative protein sequence searching by HMM-HMM alignment. *Nat Methods* 9:173-175.
61. Rock, F. L., G. Hardiman, J. C. Timans, R. A. Kastelein, and J. F. Bazan. 1998. A family of human receptors structurally related to *Drosophila* Toll. *Proc Natl Acad Sci USA* 95:588-593.
62. Roelofs, M. F., L. A. Joosten, S. Abdollahi-Roodsaz, A. W. van Lieshout, T. Sprong, F. H. van den Hoogen, W. B. van den Berg, and T. R. Radstake. 2005. The expression of toll-like receptors 3 and 7 in rheumatoid arthritis synovium is increased and costimulation of toll-like receptors 3, 4, and 7/8 results in synergistic cytokine production by dendritic cells. *Arthritis Rheum* 52:2313-2322.
63. Sarko, D., B. Beijer, R. Garcia Boy, E. M. Nothelfer, K. Leotta, M. Eisenhut, A. Altmann, U. Haberkorn, and W. Mier. 2010. The pharmacokinetics of cell-penetrating peptides. *Molecular pharmaceutics* 7:2224-2231.
64. Schneider, D. S., K. L. Hudson, T. Y. Lin, and K. V. Anderson. 1991. Dominant and recessive mutations define functional domains of Toll, a transmembrane protein required for dorsal-ventral polarity in the *Drosophila* embryo. *Genes Dev* 5:797-807.
65. Shirey, K. A., W. Lai, A. J. Scott, M. Lipsky, P. Mistry, L. M. Pletneva, C. L. Karp, J. McAlees, T. L. Gioannini, J. Weiss, W. H. Chen, R. K. Ernst, D. P. Rossignol, F. Gusovsky, J. C. Blanco, and S. N. Vogel. 2013. The TLR4 antagonist Eritoran protects mice from lethal influenza infection. *Nature* 497:498-502.
66. Silverstein, R. 2004. D-galactosamine lethality model: scope and limitations. *Journal of endotoxin research* 10:147-162.
67. Sims, J. E., C. J. March, D. Cosman, M. B. Widmer, H. R. MacDonald, C. J. McMahan, C. E. Grubin, J. M. Wignall, J. L. Jackson, S. M. Call, and et al. 1988. cDNA expression cloning of the IL-1 receptor, a member of the immunoglobulin superfamily. *Science* 241:585-589.
68. Snyder, G. A., D. Deredge, A. Waldhuber, T. Fresquez, D. Z. Wilkins, P. T. Smith, S. Durr, C. Cirl, J. Jiang, W. Jennings, T. Luchetti, N. Snyder, E. J. Sundberg, P. Wintrode, T. Miethke, and T. S. Xiao. 2014. Crystal structures of the Toll/Interleukin-1 receptor (TIR) domains from the *Brucella* protein TcpB and host adaptor TIRAP reveal mechanisms of molecular mimicry. *J Biol Chem* 289:669-679.
69. Szmacinski, H., V. Toshchakov, and J. R. Lakowicz. 2014. Application of phasor plot and autofluorescence correction for study of heterogeneous cell population. *Journal of biomedical optics* 19:046017.
70. Takeda, K., and S. Akira. 2005. Toll-like receptors in innate immunity. *Int Immunol* 17:1-14.
71. Thwaites, R., G. Chamberlain, and S. Sacre. 2014. Emerging role of endosomal toll-like receptors in rheumatoid arthritis. *Front Immunol* 5:1.
72. Toshchakov, V., B. W. Jones, P. Y. Perera, K. Thomas, M. J. Cody, S. L. Zhang, B. R. G. Williams, J. Major, T. A. Hamilton, M. J. Fenton, and S. N. Vogel. 2002. TLR4, but not TLR2, mediates IFN-beta-induced STAT1 alpha/beta-dependent gene expression in macrophages. *Nature Immunology* 3:392-398.
73. Toshchakov, V. Y., M. J. Fenton, and S. N. Vogel. 2007. Cutting Edge: Differential inhibition of TLR signaling pathways by cell-permeable peptides representing BB loops of TLRs. *J Immunol* 178:2655-2660.
74. Toshchakov, V. Y., and S. N. Vogel. 2007. Cell-penetrating TIR BB loop decoy peptides a novel class of TLR signaling inhibitors and a tool to study topology of TIR-TIR interactions.
Expert opinion on biological therapy 7:1035-1050.
75. Toshchakov, V. Y., H. Szmacinski, L. A. Couture, J. R. Lakowicz, and S. N. Vogel. 2011. Targeting TLR4 signaling by TLR4 Toll/IL-1 receptor domain-derived decoy peptides: identification of the TLR4 Toll/IL-1 receptor domain dimerization interface. *J Immunol* 186:4819-4827.
76. Ve, T., S. J. Williams, and B. Kobe. 2015. *Structure and function of Toll/interleukin-1 receptor/resistance protein (TIR) domains. Apoptosis: an international journal on programmed cell death* 20:250-261.
77. Ve, T., P. R. Vajjhala, A. Hedger, T. Croll, F. DiMaio, S. Horsefield, X. Yu, P. Lavrencic, Z. Hassan, G. P. Morgan, A. Mansell, M. Mobli, A. O'Carroll, B. Chauvin, Y. Gambin, E. Sierecki, M. J. Landsberg, K. J. Stacey, E. H. Egelman, and B. Kobe. 2017. Structural basis of TIR-domain-assembly formation in MAL- and MyD88-dependent TLR4 signaling. Nature structural & molecular biology 24:743-751.
78. Weischenfeldt, J., and B. Porse. 2008. Bone Marrow-Derived Macrophages (BMM): Isolation and Applications. *CSH Protoc* 2008:pdb prot5080.
79. Wu, Y. W., W. Tang, and J. P. Zuo. 2015. Toll-like receptors: potential targets for lupus treatment. *Acta Pharmacol Sin* 36:1395-1407.
80. Xu, Y., X. Tao, B. Shen, T. Horng, R. Medzhitov, J. L. Manley, and L. Tong. 2000. Structural basis for signal transduction by the Toll/interleukin-1 receptor domains. *Nature* 408:111-115.
81. Yamamoto, M., S. Sato, H. Hemmi, H. Sanjo, S. Uematsu, T. Kaisho, K. Hoshino, O. Takeuchi, M. Kobayashi, T. Fujita, K. Takeda, and S. Akira. 2002. Essential role for TIRAP in activation of the signalling cascade shared by TLR2 and TLR4. *Nature* 420:324-329.
82. Zanoni, I., Y. Tan, M. Di Gioia, A. Broggi, J. Ruan, J. Shi, C. A. Donado, F. Shao, H. Wu, J. R. Springstead, and J. C. Kagan. 2016. An endogenous caspase-11 ligand elicits interleukin-1 release from living dendritic cells. *Science* 352:1232-1236.
83. Zhou, Y., L. Fang, L. Peng, and W. Qiu. 2017. TLR9 and its signaling pathway in multiple sclerosis. *J Neurol Sci* 373:95-99.

The invention claimed is:

1. A Toll-like receptor (TLR)-9-specific inhibitor peptide selected from the group consisting of SEQ ID NOs:4, 6, 8, 10, 12, 21, 24, and variants thereof having a conservative amino acid change selected from an addition, a substitution, or a deletion in the Toll/IL-1 Receptor (TIR)-domain of the peptide.

2. The Toll-like receptor (TLR)-9-specific inhibitor peptide of claim 1 selected from the group consisting of SEQ ID NOs:6, 8, 10, 12, and variants thereof having a conservative amino acid change selected from an addition, a substitution, or a deletion in the TIR-domain of the peptide.

3. The peptide of claim 1 which is fused with a cell permeating peptide vector.

4. The peptide of claim 3 wherein the cell permeating peptide vector is selected from the group consisting of SEQ ID NOs:1,5, 7, 9, 11, 13, 22, 25; HSV-1 protein VP22, and HIV-1 trans-activating transcriptional activator.

5. The peptide of claim 4 which is SEQ ID NOs:1.

6. A pharmacological composition comprising a pharmaceutically acceptable excipient and the peptide of claim 1.

7. A pharmacological composition comprising a pharmaceutically acceptable excipient and the peptide of claim 5.

8. A method of inhibiting TIR:TIR interaction between two TIR (Toll/IL-1 receptor) domain-bearing proteins, comprising contacting a cell expressing TIR domain-bearing proteins with one or more peptides of claim 1.

9. A method of inhibiting TIR:TIR interaction between two TIR domain-bearing proteins, comprising contacting a cell expressing TIR domain-bearing proteins with one or more compositions of claim 6.

10. The method of claim 8, wherein the TIR domain-bearing proteins are Toll-like Receptors (TLR)s, or TLR adapter proteins, or both.

11. The method of claim 9, wherein the TIR domain-bearing proteins are TLRs, or TLR adapter proteins, or both.

12. The method of claim 8, wherein the TLR are each TLR9.

13. The method of claim 9, wherein the TLR are each TLR9.

14. The method of claim 8, wherein the TLR adapter protein are each Toll/interleukin-1 receptor domain-containing adapter protein (TIRAP).

15. The method of claim 9, wherein the TLR adapter protein are each TIRAP.

16. A Toll-like receptor (TLR)-9-specific inhibitor peptide selected from the group consisting of SEQ ID NOs:4, 6, 8, 10, 12, 21, 24, and variants thereof having a conservative amino acid change selected from an addition, a substitution, or a deletion in the Toll/IL-1 Receptor (TIR)-domain of the peptide, wherein the peptide is fused with a cell permeating peptide vector selected from the group consisting of SEQ ID NOs:1,5, 7, 9, 11, 13, 22, 25; HSV-1 protein VP22, and HIV-1 trans-activating transcriptional activator.

17. A pharmacological composition comprising a pharmaceutically acceptable excipient and the peptide of claim 16.

* * * * *